(12) United States Patent
McIntyre et al.

(10) Patent No.: US 7,579,009 B2
(45) Date of Patent: Aug. 25, 2009

(54) WHOLE BACTERIAL CELLS AS IMMUNE MODULATOR

(75) Inventors: Graham McIntyre, West Wickham (GB); John Lawson Stanford, Near Tonbridge (GB); Cynthia Ann Stanford, Near Tonbridge (GB); Oscar Adelmo Bottasso, Coronel Bogado (AR)

(73) Assignee: University College London, London (GB)

( * ) Notice: Subject to any disclaimer, the term of this patent is extended or adjusted under 35 U.S.C. 154(b) by 0 days.

(21) Appl. No.: 10/526,228

(22) PCT Filed: Sep. 5, 2003

(86) PCT No.: PCT/GB03/03873

§ 371 (c)(1),
(2), (4) Date: Nov. 16, 2005

(87) PCT Pub. No.: WO2004/022093

PCT Pub. Date: Mar. 18, 2004

(65) Prior Publication Data

US 2006/0134136 A1    Jun. 22, 2006

(30) Foreign Application Priority Data

Sep. 6, 2002 (GB) ................... 0220809.8
Jul. 22, 2003 (GB) ................... 0317144.4

(51) Int. Cl.
*A61K 39/02* (2006.01)
*A61K 49/00* (2006.01)

(52) U.S. Cl. .................. 424/234.1; 424/9.1; 424/9.2; 424/93.1; 424/93.4; 424/184.1; 424/278.1; 424/282.1; 435/243; 435/252.1; 435/253.2

(58) Field of Classification Search .............. 424/9.1, 424/9.2, 184.1, 234.1, 278.1, 282.1, 93.1, 424/93.4; 435/243, 252.1, 253.2
See application file for complete search history.

(56) References Cited

U.S. PATENT DOCUMENTS 4,599,310 A * 7/1986 Matson et al. ............. 435/71.3
5,759,992 A   6/1998 Platt

FOREIGN PATENT DOCUMENTS

| WO | WO 98/39025 | 9/1998 |
| WO | WO 99/05304 | 2/1999 |
| WO | WO 02/32455 | 4/2002 |
| WO | WO 03/101399 | 12/2003 |

OTHER PUBLICATIONS

Kang et al., "Th1 and Th2 Cytokine Responses to Academic Stress," *Research in Nursing & Health*, vol. 24, p. 245-257 (2001).
Manabe et al., "Naturally Attenuated, Orally Administered *Mycobacterium microti* as a Tuberculosis Vaccine Is Better than Subcutaneous *Mycobacterium bovis* BCG." *Infection and Immunity*, vol. 79, No. 3, p. 1566-1570 (2002).
Sharpe et al., "Single Oral Immunization with Replication Deficient Recombinant Adenovirus Elicits Long-Lived Transgene-Specific Cellular and Humoral Immune Response." *Virology*, 293, p. 210-216 (2002).
Prescott et al., "Assessment of the immunogenic potential of *Rhodococcus equi* virulence associated protein (VapA) in mice," *Veterinary Medicine*, vol. 56, pp. 213-225 (1997).
Takai et al., "Live virulent *Rhodococcus equi*, rather than killed or avirulent, elicits protective immunity to *R. equi* infection in mice," *FEMS Immunology and Medical Microbiology*, vol. 24, pp. 1-9 (1999).
Yarkoni & Rapp, "Immunotherapy of Guinea pigs with a transplanted hepatoma: comparison of intralesionary injected emulsions containing heat-killed *Nocardia rubra*, *Mycobacterium bovis* (BCG) and *Mycobacterium phlei*," *Oncology*, vol. 39, pp. 314-318 (1982).
Chambers et al., "Association of bovine papillomavirus with equine sarcoid," *J. Gen. Virol.*, vol. 84, pp. 1055-1062 (2003).
Nasir et al., "Screening for bovine papillomavirus in peripheral blood cells of donkeys with and without sarcoids," *Res. Vet. Sci.*, vol. 63, pp. 289-290 (1997).
NCIMB search results at http://www.ncimb.com/results.php?parent=culture.
Ikeda-Fugital et al., "Possible existence of a novel amphipathic immunostimulator in the phenol-water extracts of Mycobacteriaceae," *Microbiol. Immunol.*, Vo. 31(4), pp. 289-311 (1987).

* cited by examiner

*Primary Examiner*—Rodney P. Swartz
(74) *Attorney, Agent, or Firm*—Steptoe & Johnson LLP

(57) ABSTRACT

An immune modulator composition and/or pharmaceutical composition comprising a whole cell of a bacterium from the genera *Rhodococcus*, *Gordonia*, *Nocardia*, *Dietzia*, *Tsukamurella* and *Nocardioides*, wherein said immune modulator composition in use modifies a cellular immune response.

17 Claims, 21 Drawing Sheets

WHOLE BACTERIAL CELLS AS IMMUNE MODULATOR

This application claims priority under 35 USC 365(c) to International Application No. PCT/GB2003/003873, filed on Sep. 5, 2003, which claims priority to GB Patent Application No. 0220809.8, filed on Sep. 6, 2002 and GB Patent Application No. 0317144.4, filed Jul. 22, 2003.

FIELD OF THE INVENTION

The present invention relates to immune modulators, in particular vaccines that modulate a cellular immune response and uses thereof.

BACKGROUND TO THE INVENTION

Vaccines and other immune modulators have a major impact in reducing morbidity and mortality from disease. The primary immunity elicited by most current vaccines appears to be mediated by the humoral immune response. For diseases that may require a cellular immune response, such as tuberculosis and leishmaniasis, there are currently no available vaccines that are uniformly effective.

Typically, adjuvants are added to vaccines. The role of the adjuvant is to enhance the body's immune response to specific antigens of the vaccine. Commonly used adjuvants typically produce a humoral immune response but not a cell-mediated immune response. In addition, aluminium adjuvants for example may cause negative side effects, such as sterile abscesses, erythema, swelling, subcutaneous nodules, granulomatous inflammation and contact hypersensitivity.

A vaccine or other immune modulator is sought that modifies a cellular immune response and in particular the T helper cell response, for example, the T helper cell 1 (Th1) and T helper cell 2 (Th2) response.

SUMMARY OF THE INVENTION

From birth to death the immune system is educated, constantly stimulated and regulated through contact with the environment. Modern urbanization and public health measures to prevent infectious disease have virtually eliminated this exposure leading to an unprecedented rise in diseases—such as allergies and neoplastic diseases. Restoring the beneficial affects of the environment through the use of killed suspensions of harmless beneficial environmental bacteria may redress the normal balance of the immune system thus acting, therapeutically and/or prophylactically in the treatment of diseases and/or in promoting a healthy immune system.

Accordingly, the present invention is predicated upon the surprising finding that a whole cell of a bacterium from any one of the actinomycete genera *Rhodococcus, Gordonia, Nocardia, Dietzia, Tsukamurella* and *Nocardioides* administered to a test subject can elicit a modification of the immune system, in particular the cellular immune system of that test subject.

The phrase "cellular immune system", as used herein, includes a cell-mediated immune response which depends upon the presence of T lymphocytes. The term "T lymphocytes" includes cytotoxic T lymphocytes, helper T cells, suppresser T cells and regulatory T cells. Modification of a cell-mediated immune response may be used, for example, to overcome cell-mediated immune disorders including, for example an immune system imbalance and immune hypersensitivity.

The terms "modulate", "modify", "modification" and other derivatives thereof, as used herein, mean downregulating, inhibiting, inducing, stimulating, upregulating, altering or otherwise affecting a component or components of the cellular immune system.

DETAILED ASPECTS OF THE PRESENT INVENTION

In one aspect, the present invention provides an immune modulator composition comprising a whole cell of a bacterium from the genera *Rhodococcus, Gordonia, Nocardia, Dietzia, Tsukamurella* and *Nocardioides*.

The term "immune modulator", as used herein, means a substance which modulates a cellular immune system of a subject.

The term "whole cell", as used herein, means a bacterium which is intact, or substantially intact. In particular, the term "intact" as used herein means a bacterium which is comprised of all of the components present in a whole cell, particularly a whole, viable cell, and/or a bacterium which has not been specifically treated to remove one or more components from it. By the term "substantially intact" as used herein it is meant that although the isolation and/or purification process used in obtaining the bacterium may result in, for example, a slight modification to the cell and/or in the removal of one or more of the components of the cell, the degree to which such a modification and/or removal occurs is insignificant. In particular, a substantially intact cell according to the present invention has not been specifically treated to remove one or more components from it.

Although it has been suggested that individual components of bacterial cells could be used to elicit an adjuvant effect, prior to the present invention the use of whole cells of bacterium from the genera *Rhodococcus, Gordonia, Nocardia, Dietzia, Tsukamurella* and *Nocardioides* to modulate a cellular immune response was not contemplated. Surprisingly, it has been found that by using a whole cell of a bacterium from said genera, modulation of a cellular immune system can be effected. The modulation of a cellular immune response caused by administration of said whole cell of said bacterium may be advantageously long lasting as compared with the response elicited by administration of an individual component of the bacterium.

Preferably, the composition according to the present invention comprises more than one whole cell, and more preferably comprises a plurality of whole cells.

In a further aspect, the present invention provides an immune modulator composition comprising a whole cell of a bacterium from the genera *Rhodococcus, Gordonia, Nocardia, Dietzia, Tsukamurella* and *Nocardioides*, which immune modulator composition in use modifies a cellular immune response.

In another aspect, the present invention provides an immune modulator composition comprising an antigen and an adjuvant, wherein said adjuvant comprises a whole cell of a bacterium from the genera *Rhodococcus, Gordonia, Nocardia, Dietzia, Tsukamurella* and *Nocardioides*.

In another aspect, the present invention provides a pharmaceutical composition comprising a whole cell of a bacterium from the genera *Rhodococcus, Gordonia, Nocardia, Dietzia, Tsukamurella* and *Nocardioides* and optionally a pharmaceutically acceptable carrier, diluent or excipient, which immune modulator composition in use modifies a cellular immune response.

The present invention yet further provides a process of preparation of a pharmaceutical composition of the present invention, said process comprising admixing one or more of the compounds of the present invention with a pharmaceutically acceptable diluent, excipient or carrier.

In a further aspect, the present invention provides an immune modulator composition and/or a pharmaceutical composition comprising a whole cell of a bacterium from the genera *Rhodococcus, Gordonia, Nocardia, Dietzia, Tsukamurella* and *Nocardioides*, and at least one antigen or antigenic determinant.

Suitably, the antigen or antigenic determinant may be an antigen or antigenic determinant from one or more of the following: BCG (bacillus of Calmette and Guerin) vaccine, diphtheria toxoid vaccine, diphtheria/tetanus/pertussis (DTP or Triple) vaccine, pertussis vaccine, tetanus toxoid vaccine, measles vaccine, mumps vaccine, rubella vaccine, OPV (oral poliomyelitis vaccine), *Mycobacterium vaccae*, or part thereof (as taught in GB0025694.1) and a generic *plasmodium* antigen, for example a malaria parasite antigen.

Suitably, the immune modulator composition and/or pharmaceutical composition may comprise two or more such antigens or antigenic determinants.

In another aspect, the present invention provides an immune modulator composition comprising an antigen or an antigenic determinant and an adjuvant, wherein said antigen or antigenic determinant comprises a whole cell of a bacterium from the genera *Rhodococcus, Gordonia, Nocardia, Dietzia, Tsukamurella* and *Nocardioides*.

When it is the case that whole cell of the bacterium functions as an antigen or antigenic determinant the composition may suitably comprise at least one, preferably at least two, more preferably at least three, further antigens or antigenic determinants.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of one or more of an infection (eg. a bacterial, viral, for example an infection caused by papilloma viruses, including equine sarcoid, genital warts and dysplasia of the uterine cervix that precedes carcinoma of the cervix, or parasitic infection, for example, malaria, trypanosomiasis, leishmaniasis and toxoplasmosis) and/or the immunological abnormalities accompanying an infection, stress, for example, major trauma stress, psychosocial stress and chronic stress, an allergy (eg. asthma including allergic asthma, hayfever, allergic dermatitis (eczema), anaphylactic shock, allergies to plant contact or ingestion, stings—such as nettle and insect stings, and allergies to insect bites—such as midges, for instance *Culicoides* (which causes sweet-itch in horses)), heaves, COPD and cancer (for example melanoma or adenocarcinoma; an immune system imbalance (eg. an immune system imbalance in children and the elderly) and post-operative stress and infection. An immune system imbalance in the elderly may be referred to as immunosenescence.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of one or more viral infections, for example an infection caused by papilloma viruses, including equine sarcoid, genital warts and dysplasia of the uterine cervix that precedes carcinoma of the cervix. In one aspect, the present invention provides an immune modulator composition and/or a pharmaceutical composition comprising a whole cell of a bacterium from the genera *Rhodococcus, Gordonia, Nocardia, Dietzia, Tsukamurella* and *Nocardioides*, and at least one antigen or antigenic determinant, wherein said antigen or antigenic determinant is a viral antigen of bovine papilloma viruses.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of one or more of a parasitic infection, such as, for example, malaria, trypanosomiasis, leishmaniasis and toxoplasmosis.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of stress, such as, for example, major trauma stress, psychosocial stress and/or chronic stress.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of one or more of asthma (including allergic asthma), hayfever, allergic dermatitis (eczema), anaphylactic shock, allergies to plant contact or ingestion, stings—such as nettle and insect stings, and allergies to insect bites—such as midges for instance *Culicoides* (which causes sweet-itch in horses). Preferably, the immune modulator composition or pharmaceutical composition comprising a whole cell of a bacterium from the genera *Rhodococcus, Gordonia, Nocardia, Dietzia, Tsukamurella* and *Nocardioides*, is used in the manufacture of a medicament for the treatment or prevention of asthma including allergic asthma, and allergies to insect bites—such as midges for instance *Culicoides* (which causes sweet-itch in horses).

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of one or more of heaves and/or COPD, particularly in horses.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of melanoma and/or adenocarcinoma.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of an immune system imbalance in the elderly. Typically, an immune modulator composition or a pharmaceutical composition according to this aspect of the present invention may be an immune enhancer.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for enhancing the immune system which may result in for example, enhancement of growth or an increase in the efficiency of feed utilization. Typically, the immune modulator composition or pharmaceutical composition according to this aspect of the present invention may be an immune enhancer. Advantageously, the immune modulator composition or pharmaceutical composition of the present invention may be used to replace antibiotics that are currently used to promote the growth of livestock. Suitably, the immune modulator composition of the present invention may be used either alone or in combination with other treatments. The term "livestock", as used herein refers to any farmed animal. Preferably, livestock is one or more of poultry, pigs (including piglets), sheep (including lambs), cows or bulls (including calves). More preferably, livestock means pigs—including piglets.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of post-operative stress or post-operative infection.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of an immune system imbalance in children.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides*, in the manufacture of a medicament for the treatment or prevention of an adverse reaction to childhood vaccines—such as whooping cough vaccinations and the current MMR vaccinations—and/or consequences thereof. The term "adverse reaction", as used herein, means a local or generalised disadvantageous response caused by or primed by the vaccine or the administration thereof, which typically occurs within a short time-frame but which can be delayed (for example by 6-months). An "adverse reaction" may include death of the child. The adverse reaction may be caused as a consequence of a separate event, the response to which has been negatively primed by the vaccine or the administration thereof.

The present invention further provides the use of an immune modulator composition or a pharmaceutical composition comprising a whole cell of a bacterium from the genera *Rhodococcus, Gordonia, Nocardia, Dietzia, Tsukamurella* and *Nocardioides* in the manufacture of a medicament for modifying a cellular immune response.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use as a medicament.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in or as a vaccine.

Suitably, the vaccine may be a prophylactic vaccine or a therapeutic vaccine.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use as an immune enhancer.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of one or more of an infection (e.g. a bacterial, viral, for example an infection caused by papilloma viruses, including equine sarcoid, genital warts and dysplasia of the uterine cervix that precedes carcinoma of the cervix, or parasitic infection, for example, malaria, trypanosomiasis, leishmaniasis and toxoplasmosis) and/or the immunological abnormalities accompanying an infection, stress, for example, major trauma stress, psychosocial stress and chronic stress, an allergy (e.g. asthma including allergic asthma, hayfever, allergic dermatitis (eczema), anaphylactic shock, allergies to plant contact or ingestion, stings—such as nettle and insect stings, and allergies to insect bites—such as midges, for instance *Culicoides* (which causes sweet-itch in horses)), heaves, COPD and cancer (for example melanoma or adenocarcinoma, or virally related cancers such as cervical cancers for example); an immune system imbalance (e.g. an immune system imbalance in children and the elderly) and post-operative stess and post-operative infection.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of a parasitic infection, such as, for example, one or more of malaria, trypanosomiasis, leishmaniasis and toxoplasmosis.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocoardioides* for use in the treatment or prevention of a viral infection, for example an infection caused by papilloma viruses, including equine sarcoid, genital warts and dysplasia of the uterine cervix that precedes carcinoma of the cervix.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of stress, such as, for example, one or more of major trauma stress, psychosocial stress and chronic stress.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of one or more of asthma (including allergic asthma), hayfever, allergic dermatitis (eczema), anaphylactic shock, allergies to plant contact or ingestion, stings—such as nettle and insect stings, and allergies to insect bites—such as midges for instance *Culicoides* (which causes sweet-itch in horses). Preferably, the immune modulator composition or a pharmaceutical composition comprising a whole cell of a bacterium from the genera *Rhodococcus, Gordonia, Nocardia, Dietzia, Tsukamurella* and *Nocardioides* is for use in the treatment or prevention of asthma, including for example allergic asthma, and allergies to insect bites—such as midges, for instance *Culicoides* (which causes sweet-itch in horses).

In a further aspect, the present invention provides an immune modulator composition or a pharmaceutical composition comprising a whole cell of a bacterium from the genera

*Rhodococcus, Gordonia, Nocardia, Dietzia, Tsukamurella* and *Nocardioides* for use in the treatment or prevention of one or more of heaves and/or COPD, particularly in horses.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of cancer (for example melanoma and/or adenocarcinoma and/or virally related cancers such as cervical cancer for example).

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of an immune system imbalance, particularly immunosenescense, in the elderly.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of post-operative stess and infection.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in enhancing the immune system which may result in for example, enhancement of growth or an increase in the efficiency of feed utilization in, for example, livestock.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of an immune system imbalance in children.

In a further aspect, the present invention provides an immune modulator composition or a pharmaceutical composition comprising a whole cell of a bacterium from the genera *Rhodococcus, Gordonia, Nocardia, Dietzia, Tsukamurella* and *Nocardioides* for use in the treatment or prevention of an adverse reaction to childhood vaccines—such as whooping cough vaccinations and the current MMR vaccinations—and/or consequences thereof.

In another aspect, the present invention provides the use of a whole cell of a bacterium from the genera *Rhodococcus, Gordonia, Nocardia, Dietzia, Tsukamurella* and *Nocardioides* in a vaccine or a medicament, wherein said whole cell of said bacterium modifies a cellular immune response.

In one aspect, the whole cell of the bacterium according to the present invention may downregulate a Th2 response.

In another aspect, the whole cell of the bacterium according to the present invention may upregulate a Th1 response.

Suitably, the whole cell of the bacterium according to the present invention may downregulate a Th2 response and upregulate a Th1 response.

Alternatively, the whole cell of the bacterium according to the present invention may upregulate a Th1 response whilst not affecting a Th2 response.

Alternatively, the whole cell of the bacterium according to the present invention may downregulate a Th2 response, whilst also downregulating a Th1 response.

Alternatively, the whole cell of the bacterium according to the present invention may upregulate a Th2 response, whilst also upregulating a Th1 response.

By way of example only, any one or more of the following organisms may enhance Th1 response, without changing the Th2 response: *Rhodococcus ruber, Rhodococcus rhodocrous, Dietzia maris* and *Gordonia terrae*.

By way of example only, any one or more of the following organisms may enhance the Th1 response, or leave the Th1 response unchanged, and down-regulated the Th2 response: *Gordonia bronchialis, Tsukamurella inchonensis, Gordonia amarae* and *Nocardia asteroides*.

By way of example only, *Rhodococcus coprophilus* may down-regulate both Th1 and Th2 responses, suitably *Rhodococcus coprophilus* may strongly down-regulate both Th1 and Th2 responses.

In another aspect, the present invention provides a method for treating or preventing a condition in a subject comprising administering an effective amount of a pharmaceutical composition and/or immune modulator composition to a subject wherein the said composition modulates a cellular immune response.

Suitably the effective amount of the pharmaceutical composition and/or immune modulator composition may be administered as a single dose. Alternatively, the effective amount of the pharmaceutical composition and/or immune modulator composition may be administered in multiple (repeat) doses, for example two or more, three or more, four or more, five or more, ten or more, or twenty or more repeat doses.

In a further aspect of the present invention, there is provided a method for protecting, including immunizing, a subject comprising administering a pharmaceutical composition and/or immune modulator composition according to the present invention.

Preferably, a subject is protected, for example is immunized, against one or more of an infection (e.g. a bacterial, viral, for example an infection caused by papilloma viruses, including equine sarcoid, genital warts and dysplasia of the uterine cervix that precedes carcinoma of the cervix, or parasitic infection, for example, malaria, trypanosomiasis, leishmaniasis and toxoplasmosis) and/or the immunological abnormalities accompanying an infection, stress, for example, major trauma stress, psychosocial stress and chronic stress, an allergy (e.g. asthma including allergic asthma, hayfever, allergic dermatitis (eczema), anaphylactic shock, allergies to plant contact or ingestion, stings—such as nettle and insect stings, and allergies to insect bites—such as midges, for instance *Culicoides* (which causes sweet-itch in horses)), heaves, COPD and cancer (for example melanoma or adenocarcinoma or virally related cancers, such as cervical cancer); an immune system imbalance (e.g. an immune system imbalance in children and the elderly); and post-operative stess and post-operative infection.

Preferably, a subject is immunized against one or more of malaria, trypanosomiasis, leishmaniasis and toxoplasmosis.

Preferably, a subject is immunized against viral infections, for example against papilloma virus infections, including against equine sarcoid, genital warts or dysplasia of the uterine cervix that precedes carcinoma of the cervix.

Preferably, a subject is protected against stress, such as, for example, one or more of major trauma stress, psychosocial stress and chronic stress.

Preferably, a subject is protected (including immunized) against one or more of asthma (including allergic asthma), hayfever, allergic dermatitis (eczema), anaphylactic shock, allergies to plant contact or ingestion, stings—such as nettle and insect stings, and allergies to insect bites—such as midges for instance *Culicoides* (which causes sweet-itch in horses). More preferably, a subject is immunized against asthma including for example allergic asthma, and allergies to insect bites—such as midges, for instance *Culicoides* (which causes sweet-itch in horses).

Preferably, a subject is protected (including immunized) against one or more of COPD and/or heaves, particularly wherein the subject in a horse.

Preferably, a subject is protected (including immunized) against post-operative stress and infection.

Preferably, a subject is protected against the development and/or the progression of a cancer, for example melanoma and/or adenocarcinoma and/or virally related cancers such as cervical cancers for example.

Preferably, a subject is protected (including immunized) against an immune system imbalance in the elderly. In particular, the composition according to the present invention may be used to regulate the subject's immune system.

Preferably, a subject is protected (including immunized) against an immune system imbalance in children. In particular, the composition according to the present invention may be used to regulate the subject's immune system, particularly the child's immune system.

Preferably, a subject is protected (including immunized) against an adverse reaction to childhood vaccines and/or consequences thereof. In particular, the immune system of the subject is regulated, particularly a child's immune system, before and/or during and/or after administration of the childhood vaccine.

The term "protected" as used herein means that the subject is less susceptible to the disease/disorder as compared with a subject not treated or administered with the compositions according to the present invention and/or that the subject is more able to counter or overcome the disease/disorder as compared with a subject not treated or administered with the compositions according to the present invention.

In another aspect, the present invention provides administering an effective amount of a pharmaceutical composition and/or an immune modulator composition according to the present invention to a subject, wherein said composition is co-administered with an antigen or antigenic determinant.

When the composition is co-administered with an antigen or antigenic determinant in accordance with the present invention the antigen or antigenic determinant may suitably be an antigen or antigenic determinant from one or more of the following: BCG (bacillus of Calmette and Guerin) vaccine, diphtheria toxoid vaccine, diphtheria/tetanus/pertussis (DTP or Triple) vaccine, pertussis vaccine, tetanus toxoid vaccine, measles vaccine, mumps vaccine, rubella vaccine, OPV (oral poliomyelitis vaccine), *Mycobacterium vaccae*, or part thereof (as taught in GB0025694.1) and a generic *plasmodium* antigen, for example a malaria parasite antigen. Suitably two or more, or three or more, of such antigens or antigenic determinants may be co-administered with a pharmaceutical composition or an immune modulator composition according to the present invention.

Preferably, a medicament according to the present invention is used for the treatment or prevention of one or more of an infection (e.g. a bacterial, viral, for example an infection caused by papilloma viruses, including equine sarcoid, genital warts and dysplasia of the uterine cervix that precedes carcinoma of the cervix, or parasitic infection, for example, malaria, trypanosomiasis, leishmaniasis and toxoplasmosis) and/or the immunological abnormalities accompanying an infection, stress, for example, major trauma stress, psychosocial stress and chronic stress, an allergy (e.g. asthma including allergic asthma, hayfever, allergic dermatitis (eczema), anaphylactic shock, allergies to plant contact or ingestion, stings—such as nettle and insect stings, and allergies to insect bites—such as midges, for instance *Culicoides* (which causes sweet-itch in horses)), heaves, COPD and cancer (for example melanoma or adenocarcinoma or a virally related cancer such as cervical cancers for example); an immune system imbalance (e.g. an immune system imbalance in children and the elderly); and post-operative stess and post-operative infection.

Preferably, a medicament according to the present invention is used for the treatment or prevention of one or more of malaria, trypanosomiasis, leishmaniasis and toxoplasmosis.

Preferably, a medicament according to the present invention is used for the treatment or prevention of viral infections, for example papilloma virus infections, including equine sarcoid, genital warts or dysplasia of the uterine cervix that precedes carcinoma of the cervix for example.

Preferably, a medicament according to the present invention is used for the treatment or prevention of stress, such as, for example, major trauma stress, psychosocial stress and chronic stress.

Preferably, a medicament according to the present invention is used for the treatment or prevention of one or more of asthma (including allergic asthma), hayfever, allergic dermatitis (eczema), anaphylactic shock, allergies to plant contact or ingestion, stings—such as nettle and insect stings, and allergies to insect bites—such as midges, for instance *Culicoides* (which causes sweet-itch in horses). More preferably, a medicament according to the present invention is used for the treatment or prevention of asthma, including allergic asthma, and allergies to insect bites—such as midges, for instance *Culicoides* (which causes sweet-itch in horses).

Preferably, a medicament according to the present invention is used for the treatment or prevention of one or more of COPD and heaves.

Preferably, a medicament according to the present invention is used for the treatment or prevention of cancers (for example melanoma and/or adenocarcinoma and/or virally related cancers such as cervical cancers for example).

Preferably, a medicament according to the present invention is used for the treatment or prevention of an immune system imbalance in the elderly.

Preferably, a medicament according to the present invention is used for the treatment or prevention of post-operative stress or infection.

Preferably, a medicament according to the present invention is used for the treatment or prevention of an immune system imbalance in children.

Preferably, a medicament according to the present invention is used for the treatment or prevention of an adverse reaction to childhood vaccines and/or consequences thereof.

In a further aspect of the present invention, a pharmaceutical composition or an immune modulator composition according to the present invention may comprise bacteria from more than one of the genera *Rhodococcus, Gordonia, Nocardia, Dietzia, Tsukamurella* and *Nocardioides*. Suitably, the composition may comprise two or more, or three or more, bacteria from any one of the genera *Rhodococcus, Gordonia, Nocardia, Dietzia, Tsukamurella* and *Nocardioides*.

Preferably, the bacteria for use in accordance with the present invention are from the genera *Rhodococcus, Gordonia, Nocardia, Dietzia, Tsukamurella* and *Nocardioides*, including any species from any of these genera such as *Gordonia bronchialis, G. amarae, G. sputti, G. terrae, Nocardia asteroides, Dietzia maris, Tsukamurella paurometabola, Rhodococcus ruber, Rhodococcus rhodnii, R. coprophilus, Nocardioides albus* and *Tsukamurella inchonensis* for example. Suitably, the species used from each particular genus are ones which can be grown on medium, which is a low, preferably non-, antigenic medium. By way of example only, a suitable non-antigenic medium is Sauton's medium.

More preferably, the bacteria for use in accordance with the present invention are from the genus *Rhodococcus*. including *Rhodococcus ruber* (previously known as *Nocardia* rubra), *Rhodococcus rhodocrous, Rhodococcus rhodnii, Rhodococcus coprophilus, Rhodococcus opacus, Rhodococcus erythopolis*.

More preferably, the bacteria for use in accordance with the present invention is *Rhodococcus ruber*.

By way of example only, one or more of the organisms *Gordonia bronchialis, Rhodococcus ruber, Rhodococcus rhodocrous, Rhodococcus rhodnii, Dietzia maris* and *Gordonia terrae* may be effective in the treatment and/or prevention of parasitic infections.

By way of example only, one or more of the organisms *Tsukamurella inchonensis, Gordonia amarae* and *Nocardia asteroids* may be particularly effective in the treatment and/or prevention of allergies, such as allergies to insect bites—such as midges for example, and/or the treatment and/or prevention of cancers, including skin neoplams such as Equine sarcoid.

By way of example only, *Rhodococcus coprophilus* may be particularly effective in the modulation of infections, in particular parasitic infections, and/or enhancing growth in livestock.

Preferably, the bacterium according to the present invention is killed prior to use. Preferably, the bacterium according to the present invention is killed by heat-treatment thereof, for example, heat-treatment in an autoclave at 121° C. for 15 minutes. Other suitable treatments for killing the bacterium may include ultraviolet or ionizing radiation or treatment with chemicals such as phenol, alcohol or formalin.

Preferably, the bacterium according to the present invention is purified and/or isolated.

Preferably, the bacterium according to the present invention is suspended in water or buffered saline, suitably borate buffered at pH 8.

The term "subject", as used herein, means an animal. Preferably, the subject is a mammal, including for example livestock and humans. In some aspects of the present invention, the subject may suitably be a human.

The term "immune modulator" as used herein includes a vaccine.

Therapeutic Uses

The immune modulators of the present invention may be used in therapy. In particular such compounds may be used to modulate T lymphocyte responses in vivo and/or other cells involved in an immune response in vivo.

Immune modulator/pharmaceutical compositions capable of modulating, in particular blocking, T cell proliferation and/or differentiation and/or activity may be used against any disorder which is susceptible to prevention or treatment by the modulation of an adaptive immune response, i.e. a cellular immune response.

Suitably, the compositions according to the present invention are used to modulate a cellular immune response to treat or prevent one or more of an infectious disease (such as a bacterial infection eg. methycillin-resistant *Staphylococcus aureus*, tuberculosis, including multidrug resistant tuberculosis and leprosy; chronic viral infections, for example hepatitis, HIV and infections caused by papilloma viruses, including equine sarcoid, genital warts and dysplasia of the uterine cervix that precedes carcinoma of the cervix; latent viral infections, such as shingles (*Herpes zoster*) or cold sores (*Herpes simplex*) for example; or parasitic infections, for example malaria, trypanosomiasis, leishmaniasis and toxoplasmosis), an allergy, such as allergic dermatitis or allergic asthma, stress—such as major trauma stress, psychosocial stress and chronic stress, and cancer (for example, the composition may be administered regularly throughout adult life to counter the effects of tobacco).

A more extensive list of disorders is given in WO-A-98/09985. For ease of reference, part of that list is now provided: inflammation associated with hypersensitivity, allergic reactions, asthma, inflammation associated with aphthus ulceration, ulcerative colitis, hepatic fibrosis, liver cirrhosis or other hepatic diseases, dermatitis, in particular atopic dermatitis e.g. eczema, periodontal diseases or other dental diseases, to treat or ameliorate monocyte or leukocyte proliferative diseases, e.g. leukaemia, other cancers.

Infectious Diseases

Compositions capable of modulating, in particular stimulating (i.e. inducing or enhancing) T cell proliferation and/or differentiation or of preventing the induction of or reversing T cell anergy may be used generally to boost or induce T cell immune responses. Virtually all adaptive immune responses require the activation of T cells and their differentiation into cytokine-producing cells. Thus, these compositions may be used generally to prevent and/or treat infectious diseases—such as viral or bacterial. Suitably, these compositions may be used to prevent and treat parasitic infections, e.g. malaria, leishmaniasis, toxoplasmosis and trypanosomiasis). Suitably, these compositions may be used to prevent or treat viral infections, for example infections caused by papilloma viruses, including equine sarcoid, genital warts and dysplasia of the uterine cervix that precedes carcinoma of the cervix.

In one aspect of the present invention the infection is preferably trypanosomiasis.

In another aspect of the present invention the infection is preferably one caused by papilloma viruses, particularly bovine papilloma viruses 1 and 2. In a further aspect of the present invention the infection is preferably one or more of equine sarcoid, genital warts and dysplasia of the uterine cervix that precedes carcinoma of the cervix.

Equine Sarcoid

The compositions of the present invention may also be used to prevent and treat equine sarcoid.

Equine sarcoid is the commonest skin neoplasm of horses and is associated with infection with bovine papilloma viruses 1 and 2 (Chambers et al J. Gen. Virol. 2003: 84: 1055-1062). This condition is currently without an effective treatment, although surgery, non-specific immune treatment and cytotoxic drugs may all have some effect.

The compositions of the present invention are preferably administered in the same lymph node drainage area as a lesion or neoplasm.

Allergy

The compositions of the present invention may also be used to prevent and treat allergies (eg. asthma including allergic asthma, hayfever, allergic dermatitis (eczema), anaphylactic shock, allergies to plant contact or ingestion, stings—such as nettle and insect stings, and allergies to insect bites—such as midges for instance *Culicoides* (which causes sweet-itch in horses).

Sweet-itch is one of the commonest skin diseases seen in horses, particularly in wild horses and/or ponies. About 3% of horses in the U.K. are affected to some degree. Most horses show signs between 1 and 4 years of age and the condition generally worsens during summer. Certain breeds are particularly prone to the disease. Shires, Hackneys and Welsh and Icelandic ponies have all been suggested as susceptible breeds. Sweet-itch is caused by hypersensitivity to the bites of the tiny fly *Culicoides*. In the UK, the fly is present from April to October but peaks in numbers in May to September. The flies feed on the horse at specific sites usually around the tail head and under the mane. There are 20 species of *Culicoides* present in the UK and some feed underneath the horses' abdomen.

By way of example only, the compositions of the present invention may also be used to prevent and/or treat anaphylactic shock by administering a subject, which subject has a predisposition to suffer from anaphylactic shock (for instance a subject who is known to have an allergy, such as an allergy to peanuts for instance) with a composition according to the present invention, thus to reduce the subject's predisposition to anaphylactic shock should they (accidentally) come into contact with the antigen, e.g. peanuts for instance, towards which they may react adversely.

Heaves/COPD

The compositions of the present invention may also be used to prevent and treat heaves and/or COPD (Chronic Obstructive Pulmonary Disease).

Heaves is an equine lung disease with similarities to human asthma and COPD. The clinical signs in the horse are initiated by an allergic response to the particles in hay dust in lungs already damaged with a degree of fibrosis. It is most often seen in older horses (greater than six years old) that are stabled during the winter months. Hay contains microorganisms—such as bacteria and fungi as well as tiny particles of feed grains, plants, faeces, dander, and pollen. These tiny particles become aerosolised in hay dust and elicit an allergic response and fibrosis when they are inhaled by horses with heaves. The primary microorganisms believed to be involved in the etiology of heaves are *Aspergillus fumigatus*, *Thermoactinomyces vulgaris* and *Faenia rectivirgula*. Both reduction of the bronchospasm of asthma and the fibrosis of COPD are within the scope of the patent.

Stress

Stress is often presented as a symptom of modern living, the high pressure executive lifestyle, the consequences of which are widely perceived as leading to major pathological conditions such as gastric ulcers, hypertension, heart disease and strokes. Other major stressful events in life such as divorce, bereavement and moving house are seen as high risk factors for heart disease.

These are not misconceptions, the farming industry is well aware of the economic losses resulting from subjecting livestock to major stresses such as overcrowding, confinement and transportation leading to an increased susceptibility to infection and the precipitation of underlying pathology. Research by doctors and scientists is producing an increasing volume of published work showing definable stresses such as confinement can result in significant changes in endocrine (hormone) activity which subsequently can affect the body's immune functions. This can be noticeably demonstrated in major trauma stress (including surgical stress) in which the cell mediated immune response is dramatically paralyzed (Faist (1996)).

Elenkov I J (1999) report recent evidence indicating that glucocorticoids and catecholamines, the end products of the stress system, and histamine, a product of activated mast cells, might selectively suppress cellular immunity, and favour humoral immune responses. This is mediated by a differential effect of stress hormones and histamine, on Th1/Th2 patterns and type 1/type 2-cytokine production. Thus, systemically, stress might induce a Th2 shift, while, locally, under certain conditions, it might induce pro-inflammatory activities through neural activation of the peripheral corticotrophin-releasing factor-mast cell-histamine axis.

Paik (2000) in independent studies of academic stress, examined the immunological profiles of students during non exam and exam periods. They report a significant reduction in IL-2 and interferon gamma production and an increase in IL-6. This indicates that the body's immune system responds to stressful episodes by a down regulation of Th-I cytokines and a selective up-regulation of the Th2 cytokines.

Iwakabe (1998), using a mouse model of restraint stress, reports the skewing of the immune response towards Th2 dominant immunity.

This stress hormone induced switch towards Th2 immune imbalance is also reported in non major, chronic stress situations such as psychosocial stress amongst workers overwintering at the Australian National Antarctic Research Expedition stations, (Mehta (2000)). They also report an associated increase in latent virus reactivations.

Similar stress hormone and immunological changes are reported from chronic stress in care givers of dementia patients (Bauer (2000)) and in astronauts during the Euromir 95 mission (Norbiato (1998)). Of particular concern was the astronauts increased susceptibility to infection.

The body is designed to recover from stress and in acute stress clearly does as the risk of infection recedes with the patient's recovery from the major trauma.

Chronic stress however appears to maintain the Th2 dominated immune imbalance. This is a very serious consequence as all of the quoted authors allude to stress through the above mechanisms, possibly influencing the onset and/or course of infectious, inflammatory, allergic and neoplastic diseases.

This consequence is further supported by Lawrence (2000).

An immunoregulator, preferably, an orally administered immunoregulator, according to the present invention, which stimulates the Th1 response and down regulates Th2 may restore the healthy balance of the immune system and thus reduce the increased risk of serious illness associated with chronic stress.

Preferably, the composition according to the present invention is used to treat and/or prevent stress, in particular major trauma stress, psychosocial stress and chronic stress.

Preferably, the composition according to the present invention is used to treat and/or prevent stress in animals, suitably in humans and/or livestock.

Immune System Imbalance

An immune system imbalance—such as an upregulation, downregulation or inappropriately regulated cellular immune response—may occur at any time in the life of a subject. Suitably, the compositions may be used to modulate an immune system imbalance. That is to say, the compositions according to the present invention may be used to treat and/or prevent an immune system imbalance.

(a) In Children

Suitably, the immune modulator composition or a pharmaceutical composition may be used to modulate an immune system imbalance, in children, including babies, infants and juveniles. An immune system imbalance—such as an upregulation, downregulation or inappropriately regulated cellular immune response—may occur in children following vaccination, for example following childhood vaccinations. Such an immune system imbalance may result in conditions such as the onset of allergies, i.e. allergic dermatitis and allergic asthma.

With the aim of protecting children from infections, repeated injections against Diptheria, Tetanus, Pertussis, Polio, Measles, Mumps and the Rubella are given. All of these are judged necessary and pressure is exerted by health authorities to ensure that children are presented for vaccination at the appropriate time. However, most vaccinations given in early life contain an alum adjuvant, which has important immunological consequences. Alum is a potent stimulus to the Th2 pattern of response and the consequential immune dysregulation causes the child to become vulnerable to the development of allergies and possibly cancer for example.

It is possible to re-educate the immune system to a proper recognition, regulation and response both to self and to the rest of the world.

Suitably, the immune modulator composition or a pharmaceutical composition may also be used for the treatment or prevention of an adverse reaction to childhood vaccines—such as whooping cough vaccinations and the current MMR vaccinations—and/or consequences thereof.

(b) Immune System Imbalance in the Elderly

An immune system imbalance—such as an upregulation, downregulation or inappropriately regulated cellular immune response, in particular downregulation, for example a deterioration of immune function—may occur in older people, generally in excess of 60 years. In elderly people, a downregulation in the cellular immune response is generally referred to as immunosenescence. Typically, the deterioration of immune function may lead to increased susceptibility to infectious diseases and neoplasia for example. The number of old people as a proportion of the population is dramatically increasing and geriatric medicine is becoming an important aspect of clinical practice. It is not surprising therefore that research has focused on the mechanisms of immunosenescence and the links between the health of the immune system and longevity. Goronzy (2001), examined the varying efficacy of influenza vaccination in the elderly. In this study, only 17% of subjects showed a rise in titre to all 3 haemagglutinins (successful vaccination) 1 month following vaccination and that 46% showed no demonstrable response at all. It was proposed that responsiveness to influenza vaccination is a useful biological marker of immunosenescence. A number of researchers have studied various aspects of the immune function in the elderly. For example, Lio (2000) studied cytokine responses, Solana (2000) studied NK and NKt cells, and Ginaldi (1999) suggested that a Th1 to Th2 cytokine production shift and an increased production of proinflammatory cytokines could explain many aspects of age-associated pathological events, such as atherosclerosis and osteoporosis. Accordingly, a non-pathological stimulation of the immune system which drives the cytokine response away from the proinflammatory Th2 towards Th1 is required. Preferably, such an immune modulator reduces the mortality from acute infection, counters the onset and reduces the morbidity of age related autoimmune disease and possibly reduces the rate of neoplastic disease, all of which are associated with immunosenescence.

Typically, an immune modulator composition or a pharmaceutical composition according to this aspect of the present invention may be an immune enhancer.

The potential role of probiotic commensal gut or dairy bacteria have been investigated in this area. For example, milk products supplemented with $5 \times 10^9$ or $5 \times 10^{10}$ *Bifidobacterium lactis* or *Lactobacillus rhamnosus* per dose taken daily for 3 weeks has been reported to increase the numbers of peripheral blood NK, CD4 and CD25 cells and generally boost systemic cellular immunity in the elderly (Gill, (2001)).

Currently a number of products containing high numbers of Lactobacilli and other intestinal commensal flora are being actively promoted as "lifestyle enhancers". A review by Sanders (2001), on the claimed probiotic effects of *Lactobacillus acidophilus*, available as a drug since 1950, suggests its effects require further validation and clarification of the mechanism of action. Whilst there is a beneficial effect from replacing the bowel flora after diarrhoeal disease and combating candidiasis following antibiotic therapy, immune stimulation appears unreliable and short lived. However, this work clearly identifies a role for a potent orally administered immune modulator, preferably killed so as to avoid the difficulties of maintaining live products.

Oral vaccination is a long established successful mechanism for inducing local protective immunity against oral/faecal pathogens—such as polio. However, orally administered vaccines have also been shown to evoke systemic protective immune responses both cell mediated and humoral.

Kim (2001) showed that feeding with Japanese cedar pollen produced oral tolerance to specific allergy induced by subsequent injection of pollen in oil. This was associated with decreased specific immunoglobin levels and a significant reduction in interleukin-4 production ie the TH2 response was down-regulated.

Therefore, a systemic immune response may be both stimulated and modulated by administration—such as oral administration—of a suitable immune modulator.

Suitably, in one aspect of the present invention it is envisaged that a whole cell of the bacterium according to the present invention, may be included in food preparations and/or may be supplied as a type of "remedy", preferably orally.

Enhancing the Immune System

The compositions of the present invention may be used in the manufacture of a medicament for enhancing the immune system in an animal, preferably a mammal, more preferably livestock, which may result in for example, enhancement (e.g. promotion) of growth and/or an increase in the efficiency of feed utilization and/or a generally increased well-being (i.e. the overall health of the subject is improved) in the subject. The overall health of a subject can be determined by one or more of the following parameters for example: weight data (with weight gain being a positive determinant), alertness (with full alert being a positive determinant), movement (with energetic movement as opposed to lethargic movement being a positive determinant) and sickness (with reduced amount of sickness being a positive determinant). Typically, the immune modulator composition or pharmaceutical composition according to this aspect of the present invention may be an immune enhancer.

Advantageously, the immune modulator composition or pharmaceutical composition of the present invention may be used to replace antibiotics that are currently used to promote the growth of livestock.

The term "livestock", as used herein refers to any farmed animal. Preferably, livestock is one or more of poultry (including chickens), pigs (including piglets), sheep (including lambs), cows or bulls (including calves). More preferably, livestock means pigs—including piglets.

The present invention also contemplates the genera of the present invention being administered in combination with known probiotic bacteria, for modification of the cellular immune response.

Commercially at present antibiotics are commonly used as dietary enhancing feed additives (or growth promoters) and are incorporated into animal feed. However, the EU, is expected to introduce a complete ban on the non-clinical use of antibiotics in animal husbandry. Therefore, the market requires effective alternatives.

An advantage of the present invention is that it may be used (optionally together with good animal husbandry practices) as a replacement to dietary enhancing feed additive (or growth promoters).

The immune modulator compositions or pharmaceutical compositions of the present invention may be administered as a food additive when used to enhance the immune system.

Cancer

Suitably, the compositions according to the present invention are used to modulate a cellular immune response to treat and/or prevent cancer. In particular it is envisaged that the compositions according to the present invention may be used to protect a subject against developing and/or the progression of a cancer. In particular, the subject with a modulated cellular immune response may be less susceptible to the development of cancer.

In particular, during cancer growth an unregulated increase in Th2 is observed.

Cancer is a disease that affects many people, with 65 percent of cases occurring in those over 65. As the average life expectancy in the UK has almost doubled since the mid-nineteenth century, the population at risk of cancer has grown. Death rates from other causes of death, such as heart disease, have fallen in recent years while deaths from cancer have remained relatively stable. The result is that 1 in 3 people will be diagnosed with cancer during their lifetime and 1 in 4 people will die from cancer.

Examples of cancer include bladder, brain tumor, breast cancer, cervical cancer, colon and rectal cancer, adenocarcinoma, endometrial cancer, esophageal cancer, kidney cancer, leukaemia, liver cancer, lung cancer, melanoma, myeloma, non-hodgkin's lymphoma, ovarian cancer, pancreatic cancer, prostate cancer, sarcoma, soft tissue and stomach cancer.

In addition, persistent smoking of tobacco, and to a lesser, extent passive smoking, has been associated with carcinomas of the parts directly in contact with smoke, oropharynx, trachea, lungs, oesophagus and stomach. As well as these, distant tumours such as those of the kidney, bladder, pancreas, liver and myeloid leukaemia may be increase by smoking of tobacco. In the present invention, it is envisaged that compositions according to the present invention could be administered to smokers of tobacco in an attempt to reduce the smokers' risk of developing carcinomas associated with tobacco smoking.

Suitably, the cancer may be an adenocarcinoma or a melanoma.

Suitably, the cancer may be virally related cancers such as cervical cancer for example. Without wishing to be bound by theory, in some instances it has been found that an infection caused by papilloma viruses, such as dysplasia of the uterine cervix, precedes carcinoma of the cervix. Thus, cervical cancer is herein considered a "virally related cancer". However, the term "virally related cancer" as used herein means any cancer which may be caused by or related with a viral infection.

Post-Operative Recovery Stress and Infection

Following any major operation a number of situations potentially arise:—

Stresses associated with a surgical operation include one or more of the following: apprehension before the operation, stress to the tissues due to the operative procedures, the pain usually accompanying recovery, worry about the significance of operative findings.

These kinds of stress are associated with the deviation of T-cell function towards Th2, immunosuppressive effects of premedication and anaesthetics, which may persist for days or weeks after the operation itself.

In addition, exposure of cut flesh to direct infection at the time of operation and of the wound to infection in the recovery room and wards prior to leaving hospital is also a problem.

A combination of these factors exposes the patient to a series of potential bacterial infections, which:—

Since the patient is hospitalized, include such notorious hospital-associated infections as those with methicillin-resistant-*Staphylococcus aureus* (MRSA). Operations on the bowel expose the patient to gram-negative infections due to exposure of cut tissues to bowel contents. Operations on the lower limbs are also subject to infections with normal members of the gut flora.

Minor infections of the wound delay healing and increase the chances of contracting more serious infections.

To counteract these influences, immune regulation towards Th1 and a down-regulation of Th2 a result of the application of the invention, should do one or more of the following: increase non-specific resistance to post-operative bacterial infections; aid in wound healing and/or reduce stress.

T Helper Cells

The term 'Th1' as used herein refers to a type I T-helper cell (Th1). The term may also be used herein to refer to the response mediated by or through such a cell type. Such a response may include one or more of the secretion of Interleukin-2 (IL-2), the secretion of Interferon-gamma (IFN-γ), activation of macrophages, activation of cytotoxic T-cells, or any other Th1-associated event. Thus, the term 'Th1' may include Th1 cell(s) as well as the immune response(s) which such cell(s) produce.

The term 'Th2' as used herein refers to a type 2 T-helper cell (Th2). The term may also be used herein to refer to the response mediated by or through such a cell type. Such a response may include one or more of the secretion of Interleukin-4 (IL-4), the secretion of the splice variant interleukin IL-4δ2, the secretion of Interleukin-5 (IL-5), increase in levels of cell determinant 30 (CD30) on lymphocytes, increase in levels of Immunoglobulin-E (IgE) in the blood or eosinophils in the blood, or any other Th2-associated event. Thus, the term 'Th2' may include Th2 cell(s) as well as the immune response(s) which such cell(s) produce.

It is known that various conditions may result in or from an unregulated or inappropriately regulated cellular immune response, in particular in the activation and/or proliferation of Th1 and/or Th2, which if left unregulated or inappropriately regulated has been found to result in one or more detrimental effects on the subject.

In particular, such an unregulated or inappropriately regulated cellular immune response has been found to occur following vaccination, eg. following childhood vaccinations, and is thought to result in conditions such as the onset of allergies, i.e. allergic dermatitis and allergic asthma. By way of example, Lewis D *Curr Opin Immunol* 2002; 14: 644 report that Th2 immune responses mediated by the secretion of IL-4, IL-5 and IL-13 are key in the pathogenesis of atopic disorders, including allergen-induced asthma, rhinoconjunctivitis and anaphylaxis. Although such responses are down-regulated to some degree by conventional specific immunotherapy, this approach is only partially effective and has a substantial risk of adverse effects. Many strategies for immunotherapeutic prophylaxis and for treatment of atopic diseases have been devised on the basis of mouse allergy models, including the downregulation of Th2 responses by the induction of regulatory T cell activity, Th2 to Th1 immune deviation, Th1 crossregulation of Th2 immune responses, anergy and immunosuppressive cytokines. Choi & Koh *Ann Allergy Asthma Immunol* 2002; 88: 584-91 examined whether BCG vaccination of adult patients with asthma, a Th2-associated allergic disease, is clinically effective. It was shown that BCG vaccination improved lung function and reduced medication use in adults with moderate-to-severe asthma. This amelioration was accompanied by a suppressed Th2-type immune response, suggesting that BCG vaccination might be an effective therapeutic modality against asthma. von Hertzen *J Allergy Clin Immunol* 2002; 109: 923-8 outlined the possibility that prolonged maternal stress associated with sustained excessive cortisol secretion could affect the developing immune system—especially Th1/Th2 cell differentiation which may further increase the susceptibility to asthma and atopy in genetically predisposed individuals.

In addition, an unregulated or inappropriately regulated cellular immune response has been observed during disease progression. In particular during cancer growth an unregulated increase in Th2 is observed. By way of example, Maraveyas et al. *Ann Oncol* 1999; 10: 817-24 have studied the efficacy of SRL 172 vaccine in patients with cancer ie. advanced stage IV (AJCC) malignant melanoma. Induction of intracellular cytokines (IL-2 and INF-gamma) in peripheral blood lymphocytes (PBLCs) from these patients was assayed and correlated to clinical outcome. It was demonstrated that SRL 172 was effective in inducing intracellular IL-2 responses in a significant number of patients with stage IV (AJCC) melanoma. Stanford et al. *International Journal of Pharmaceutical Medicine* 1999; 13: 191-195 report that there is increasing evidence that effective anti-tumour immune responses are likely to be mediated by type I cytokines. Recent investigations indicate that heat-killed *Mycobacterium vaccae*, is a reliable Th1 adjuvant and preliminary clinical trials indicate beneficial effects in melanoma, and cancer of the prostate and lung. More extensive controlled studies are currently being conducted to confirm these findings.

An unregulated or inappropriately regulated cellular immune response has also been observed during infection and particularly chronic infection, for example during progressive tuberculosis, lepromatous leprosy, visceral leishmaniasis and HIV infection and during allergies. By way of example, Clerici & Shearer G M *Immunol Today* 1993; 14: 107-11 propose that a Th1 to Th2 switch is a critical step in the etiology of HIV infection. Clerici & Shearer *Immunol Lett* 1996; 51: 69-73 show that HIV-specific cell mediated immunity may be the main correlater of protection against HIV infection and against the progression of HIV infection to AIDS. Abbot N C et al. *European Journal of Vascular and Endovascular Surgery* 2002 24:202-8 evaluated immunotherapy as a means of improving peripheral blood flow in chronic leprosy patients by administration of heat-killed *Mycobacterium vaccae*. It was shown that immunotherapy, given 18 months earlier, significantly improved blood flow and temperature sensation, in fully-treated, chronic, leprosy patients.

Accordingly, an aim of the present invention is to promote and establish the regulation of a cellular immune response, including the regulation or modulation of Th1 and/or Th2, in such a way so as to overcome the negative effects of the unregulated or inappropriately regulated cellular immune response.

Suitably, the use of an immune modulator composition and/or pharmaceutical composition according to the present invention modulates the Th1 or Th2 response, i.e. a Th1 or Th2 response that results in, for example, tissue damage.

Suitably, the use of an immune modulator composition and/or pharmaceutical composition according to the present invention may decrease the Th1 response and decrease the Th2 response. By way of example, such an immune modulator and/or pharmaceutical composition may be useful in the treatment of diabetes for example.

Suitably, the use of an immune modulator composition and/or pharmaceutical composition according to the present invention may increase the Th1 response without affecting the Th2 response. By way of example, such an immune modulator and/or pharmaceutical composition may be useful as an immune enhancer.

Suitably, the use of an immune modulator composition and/or pharmaceutical composition according to the present invention may increase the Th1 response and decrease the Th2 response. By way of example, such an immune modulator and/or pharmaceutical composition may be useful in the treatment of asthma.

Suitably, a skilled person can test a specific species of each genus according to the present invention to determine its specific Th1/Th2 response.

An unregulated or inappropriately regulated immune response may play a role in the establishment of disease due to the fact that some diseases cause shifted Th1 and/or Th2 responses. Accompanying these atypical Th1 and Th2 reactions are a series of abnormal inflammatory responses, which may take part in the mechanisms underlying tissue pathology.

By way of example only, the immune modulator composition and/or pharmaceutical composition according to the present invention may counteract the disadvantages of reduced contact with environmental influences (for example, antigens) commensurate with modern life, may counteract the influence of treatment of an infection (eg. a parasitic infection, such as, for example, malaria, trypanosomiasis, leishmaniasis, and toxoplasmosis) and/or the immunological abnormalities accompanying an infection, stress, such as, for example, major trauma stress, psychosocial stress and chronic stress, an allergy (eg. asthma including asthma, allergic asthma, hayfever, allergic dermatitis (eczema), anaphylactic shock, allergies to plant contact or ingestion, stings—such as nettle and insect stings, and allergies to insect bites—such as midges for instance *Culicoides* (which causes sweet-itch in horses), heaves, COPD and cancer (for example melanoma or adenocarcinoma); an immune system imbalance (eg. an immune system imbalance in children eg. the undesirable effect of childhood vaccines and the elderly); and post-operative stess and post-operative infection.

Vaccines

The preparation of vaccines which contain one or more substances as an active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the active ingredient(s) encapsulated in liposomes. The active ingredients are often mixed with excipients which are pharmaceutically acceptable and compatible with the active ingredient. Suitable excipients are, for example, water, saline, dextrose, glycerol, ethanol, or the like and combinations thereof. Alternatively, the vaccine may be prepared, for example, to be orally ingested and/or capable of inhalation.

In addition, if desired, the vaccine may contain minor amounts of auxiliary substances such as wetting or emulsifying agents and pH buffering agents.

Administration

Typically, a physician will determine the actual dosage of a vaccine, immune modulator composition and pharmaceutical composition which will be most suitable for an individual subject and it will vary with the age, weight and response of the particular patient. The dosages below are exemplary of the average case. There can, of course, be individual instances where higher or lower dosage ranges are merited.

Preferably, the actual dosage that is used results in minimal toxicity to the subject.

The compositions of the present invention may be administered by direct injection. The composition may be formulated for parenteral, mucosal, intramuscular, intravenous, subcutaneous, intraocular, intradermal or transdermal administration.

Suitably, the composition according to the present invention may be administered at a dose of $10^3$-$10^{11}$ organisms, preferably $10^4$-$10^{10}$ organisms, more preferably $10^6$-10-5×$10^9$ organisms, and even more preferably $10^6$-$10^9$ organisms. Typically, the composition according to the present invention may be administered at a dose of $10^8$-$10^9$ bacteria for human and animal use.

If the compositions of the present invention are to be administrated as immune enhancers, then $10^3$-$10^{11}$ organisms per dose, preferably $10^4$-$10^{10}$ organisms per dose, more preferably $10^6$-10-5×$10^9$ organisms per dose, and even more preferably $10^6$-$10^9$ organisms per dose, and even more preferably, $10^8$-$10^9$ bacteria per dose for human and animal use may be administered at regular intervals.

As will be readily appreciated by a skilled person the dosage administered will be dependent upon the organism to which the dose is being administered.

The term "administered" includes delivery by delivery mechanisms including injection, lipid mediated transfection, liposomes, immunoliposomes, lipofectin, cationic facial amphiphiles (CFAs) and combinations thereof, or even viral delivery. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular, intradermal or subcutaneous route.

The term "co-administered" means that the site and time of administration of each of the adjuvants(s), antigen(s) and/or antigenic determinant(s) of the present invention are such that the necessary modulation of the immune system is achieved. Thus, whilst the antigen(s) and adjuvant(s) may be administered at the same moment in time and at the same site, there may be advantages in administering the antigen(s) and/or antigenic determinant(s) at a different time and to a different site from the adjuvant(s). The antigen(s) and/or antigenic determinant(s) and adjuvant(s) may even be delivered in the same delivery vehicle—and the antigen(s) and/or antigenic determinant(s) and adjuvant(s) may be coupled and/or uncoupled and/or genetically coupled and/or uncoupled. By way of example only, the immune modulator composition according to the present invention may be administered before, at the same time or post administration of one or more antigens or further antigens.

The antigen, antigenic determinant, peptide or homologue or mimetic thereof may be administered separately or co-administered to the host subject as a single dose or in multiple doses.

The immune modulator composition and/or pharmaceutical composition of the invention may be administered by a number of different routes such as injection (which includes parenteral, subcutaneous, intradermal and intramuscular injection) intranasal, mucosal, oral, intra-vaginal, urethral or ocular administration.

Preferably, in the present invention, administration is by injection. More preferably the injection is intradermal.

Preferably, in the present invention, administration is by an orally acceptable composition.

For vaccination the composition can be provided in 0.1 to 0.2 ml of aqueous solution, preferably buffered physiological saline, and administered parenterally, for example by intradermal inoculation. The vaccine according to the invention is preferably injected intradermally. Slight swelling and redness, sometimes also itching may be found at the injection site. The mode of administration, the dose and the number of administrations can be optimized by those skilled in the art in a known manner.

Antigens

As used herein, an "antigen" means an entity which, when introduced into an immunocompetent host, modifies the production of a specific antibody or antibodies that can combine with the entity, and/or modifies the relevant Th response, such as Th2 and/or Th1. The antigen may be a pure substance, a mixture of substances or soluble or particulate material (including cells or cell fragments or cell sonicate). In this sense, the term includes any suitable antigenic determinant, cross reacting antigen, alloantigen, xenoantigen, tolerogen, allergen, hapten, and immunogen, or parts thereof, as well as any combination thereof, and these terms are used interchangeably throughout the text.

The term "antigenic determinant or epitope" as used herein refers to a site on an antigen which is recognized by an antibody or T-cell receptor, or is responsible for evoking the T-helper cell response. Preferably it is a short peptide derived from or as part of a protein antigen. However the term is also intended to include glycopeptides and carbohydrate epitopes. The term also includes modified sequences of amino acids or carbohydrates which stimulate responses which recognize the whole organism.

It is advantageous if the antigenic determinant is an antigenic determinant of the infectious agent which causes the infectious disease.

A "preventative" or "prophylactic" vaccine is a vaccine which is administered to naive individuals to prevent development of a condition, such as by stimulating protective immunity.

A "therapeutic" vaccine is a vaccine which is administered to individuals with an existing condition to reduce or minimize the condition or to abrogate the immunopathological consequences of the condition.

Adjuvants

The term 'adjuvant' as used herein means an entity capable of augmenting or participating in the influencing of an immune response. An adjuvant is any substance or mixture of substances that assists, increases, downregulates, modifies or diversifies the immune response to an antigen.

The immune modulator composition and/or pharmaceutical composition according to the present invention may comprise one or more adjuvants which enhance the effectiveness of the immune modulator composition and/or pharmaceutical compositions. Examples of additional adjuvants which, may be effective include but are not limited to: aluminium hydroxide, aluminium phosphate, aluminium potassium sulphate (alum), beryllium sulphate, silica, kaolin, carbon, water-inoil emulsions, oil-in-water emulsions, muramyl dipeptide, bacterial endotoxin, lipid X, *Corynebacterium parvum* (*Propionobacterium acnes*), *Bordetella pertussis, Mycobacterium vaccae*, polyribonucleotides, sodium alginate, lanolin, lysolecithin, vitamin A, interleukins such as interleukin 2 and interleukin-12, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Only aluminium hydroxide is approved for human use. Some of the other adjuvants, such as *M. vaccae* for example, have been approved for clinical trials.

Suitably, the adjuvant may be a whole cell of a bacterium from any one of the genera *Rhodococcus, Gordonia, Nocardia, Dietzia, Tsukamurella* and *Nocardioides.*

In the art, it is known that DNA vaccines, which are essentially DNA sequences attached to gold particles and which are fired into the skin by a helium gun, are efficient vaccine delivery systems. Unlike conventional vaccines, these DNA vaccines do not require a traditional adjuvant component. In accordance with a further aspect of the present invention, the immune modulator composition as defined herein may suitably be used in conjunction with such DNA vaccines to augment or participate in the influencing of the immune response.

Pharmaceutical Compositions

The present invention also provides a pharmaceutical composition comprising a therapeutically effective amount of a whole cell of a bacterium from the genera *Rhodococcus, Gordonia, Nocardia, Dietzia, Tsukamurella* and *Nocardioides* and optionally a pharmaceutically acceptable carrier, diluent or excipients (including combinations thereof).

The pharmaceutical composition may comprise two components—a first component comprising an antigen and a second component comprising an adjuvant thereof. The first and second component may be delivered sequentially, simultaneously or together, and even by different administration routes.

Suitably, the antigen may even be engendered within the host tissues as part of a disease process. Thus, antigen may originate from a bacterial, host or parasitic invasion, or may be a substance released from the tissues such as a stress protein or a tumour antigen.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilizing agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular, intradermal or subcutaneous route. Alternatively, the formulation may be designed to be delivered by both routes.

Preferably in the present invention the formulation is of injectable form. More preferably the formulation is intradermally injected.

Preferably in the present invention the formulation is an orally acceptable composition.

Where the agent is to be delivered mucosally through the gastrointestinal mucosa, it should be able to remain stable during transit through the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly, intradermally or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Pharmaceutical Combinations

The agent of the present invention may be administered with one or more other pharmaceutically active substances. By way of example, the present invention covers the simultaneous, or sequential treatments with an immune modulator composition and/or pharmaceutical composition according to the present invention, and one or more steroids, analgesics, antivirals, interleukins such as IL-2, or other pharmaceutically active substance(s).

It will be understood that these regimes include the administration of the substances sequentially, simultaneously or together.

Immune Enhancer

The term "immune enhancer" as used herein means one or more bacteria either isolated or in culture which when administered to a subject benefit the health of that subject. Preferably, this benefit is achieved by the modification of the cellular immune response of the subject.

In accordance with the present invention, immune enhancers may be used, for example, for the treatment or prevention of an immune system imbalance in a subject, preferably a child or an elderly subject, or for enhancing the immune system of a subject, for example of a mammal, particularly of livestock or of humans.

The immune enhancers may be administered by consumption in specially designed food or in animal feeds, for example pig animal feeds supplemented with the bacteria of the present invention.

The immune enhancers may also be administered by other routes—such as direct injection.

Preferably, the bacteria are killed so as to avoid the difficulties of maintaining live products.

Identifying a Bacterium that Modulates a Cellular Immune Response

In another aspect, the present invention relates to a method for identifying one or more whole cells of bacteria from the genera *Rhodococcus, Gordonia, Nocardia, Dietzia, Tsukamurella* and *Nocardioides* that modulate (e.g. modify) a cellular immune response comprising the steps of: (a) contacting a first test animal with an immunostimulant; (b) contacting a second test animal with an immunostimulant mixed with a bacterium; (c) measuring the cellular immune response in each of the test animals; and (d) comparing the cellular immune response in each of the test animals, wherein, a lower cellular immune response from the immunostimulant mixed with a bacterium in comparison to the immunostimulant alone is indicative of a modification of the cellular immune response by the bacterium.

In another aspect, the present invention relates to a method of determining the Th1/Th2 response of a species of bacteria selected from the genera *Rhodococcus, Gordonia, Nocardia, Dietzia, Tsukamurella* and *Nocardioides* which method comprises utilization of the tuberculin skin test. In mice, the tuberculin skin test is preferably carried out on the foot pad. In a predominant Th1 reaction the positive foot pad immune response is maximal at 24 hours and diminishes at 48 hours. However, as the Th2 reactivity increases then the 48 hour positive foot pad immune response increases and can even exceed the foot pad immune response at 24 hour.

The effect of BCG vaccination is well documented using this tuberculin skin test. Thus, the test assay can be used to assess whether or not the introduction of an immune modulator composition according to the present invention modulates the BCG cellular immune response.

As used herein, the term "test animal" refers to any animal that elicits a cellular immune response to the immunostimulant. Preferably, the test animal(s) is a mammal. More preferably, the test animal(s) is a rat, hamster, rabbit, guinea pig or mouse. More preferably, the test animal(s) is a mouse.

Preferably, the bacterium modifies the T helper cell response. Suitably, the bacterium may modify the T helper cell response by decreasing the Th1 and Th2 response. Suitably, the bacterium may modify the T helper cell response by increasing the Th1 response and decreasing the Th2 response. Suitably, the bacterium may modify the T helper cell response by increasing the Th1 response without affecting the Th2 response.

Preferably, the immunostimulant will have a known Th1 and Th2 response. For example, with the immunostimulant BCG the reaction is usually largest at 24 h when it is an indicator of the Th1 response; the reaction at 48 h is usually less and includes a Th2 contribution. It is known that BCG predominantly stimulates a Th1 response. By use of such immunostimulants it may be possible to determine the Th1/Th2 response of a test bacterium and, thus, it may be possible to identify one or more bacteria which have a desired Th1/Th2 response to treat and/or prevent a particular disease and/or disorder.

Preferably, the cellular immune response is measured using the tuberculin skin test. Vaccination with an immunostimulant—such as BCG—induces a response to skin-testing with tuberculin (a soluble preparation of tubercule bacilli), when tested later. The local reaction is measured at various intervals, for example, 24 hours, 48 hours and 72 hours after injection of tuberculin. Briefly, an immunostimulant (eg. BCG) is used that induces a positive immune response to tuberculin. In the test animal, the tuberculin skin test is preferably carried out on the foot pad. In a predominant Th1 reaction the positive foot pad immune response is usually maximal at 24 hours and diminishes at 48 hours. However, as the Th2 reactivity increases then the 48 hour positive foot pad immune response increases and can even exceed the foot pad immune response at 24 hour. Thus, the assay can be used to assess whether or not the introduction of an immune modulator composition according to the present invention modulates the cellular immune response.

Preferably, the immunostimulant is BCG.

Figure 1:
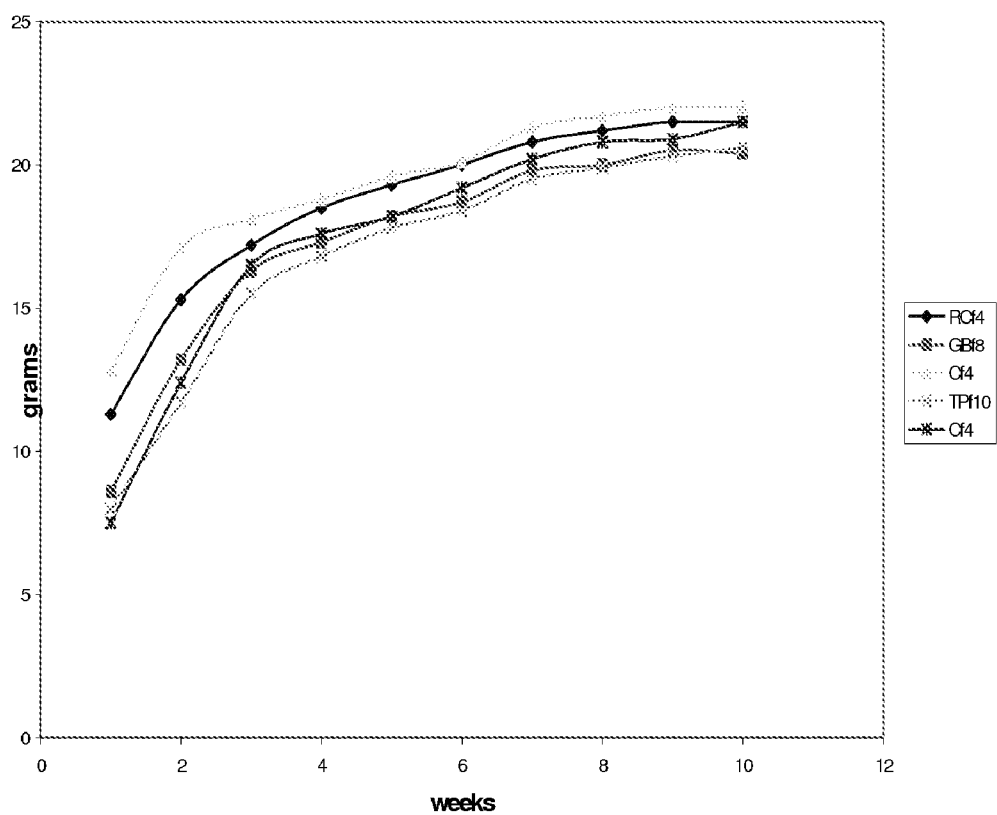
FIG. 1 is a graph demonstrating the results of weight gain means/litter females test and controls over 12 weeks from weaning.

The invention will now be further described by way of Examples, which are meant to serve to assist one of ordinary skill in the art in carrying out the invention and are not intended in any way to limit the scope of the invention.

EXAMPLES

Methods

Tuberculin Skin Test

The tuberculin skin test is an appropriate model assay to assess the effect of an immune modulator composition, i.e. bacterial compositions/suspensions comprising whole killed bacterial cells according to the present invention, on a cellular immune response.

BCG vaccination induces a positive immune response to tuberculin. In mice, the tuberculin skin test is preferably carried out on the foot pad. In a predominant Th1 reaction the positive foot pad immune response is maximal at 24 hours and diminishes at 48 hours. However, as the Th2 reactivity increases then the 48 hour positive foot pad immune response increases and can even exceed the foot pad immune response at 24 hour.

The effect of BCG vaccination is well documented using this tuberculin skin test. Thus, the test assay can be used to assess whether or not the introduction of an immune modulator composition according to the present invention modulates the BCG cellular immune response.

Preparation of a Bacterial Suspension

The bacterial species from the genera *Rhodococcus*, *Gordonia*, *Nocardia*, *Dietzia*, *Tsukamurella* and *Nocardioides* may be grown in an antigen-free medium, such as Sauton's medium, in a fermenter for 2-28 days. Alternatively, the bacterial species of interest may be grown on a solid slope. Alternative methods would be readily available to those skilled in the art.

The resulting bacterial mass may be harvested and either used directly or after washing to make a suspension in buffer. The bacterial cell suspension is prepared to contain between 100,000 and 10,000,000,000 bacilli per dose. The bacterial cells are resuspended in water or in a saline. Preferably, the saline is buffered at pH 8.0 with borate. Preferably the bacilli are inactivated (killed), suitably by heating in an autoclave for 15 minutes at 121° C. The resulting bacterial suspension comprises whole cells.

Example 1

Modulation of a Cellular Immune Response by *Rhodococcus ruber* (R.r.).

Group 1: young adult female outbred mice were left unvaccinated as a control group.

Group 2: young adult female outbred mice were vaccinated on day 0 into the scruff of the neck with BCG ($10^5$ bacilli) (Evans).

Group 3: young adult female outbred mice were vaccinated on day 0 into the scruff of the neck with BGC ($10^5$ bacilli) to which heat-killed *Mycobacterium vaccae* (M.v.) ($10^7$ bacilli) had been added.

All mice in Groups 1-3 were foot pad tested for tuberculin immune response at days 10 and 30. Then each mouse was injected with heat-killed *Mycobacterium vaccae* ($10^7$ bacilli) at day 40. At day 50 the tuberculin test on the foot pad was repeated.

Group 4: young adult female outbred mice were left unvaccinated as a further control group.

Group 5: young adult female outbred mice were vaccinated on day 0 into the scruff of the neck with BCG (Evans) ($10^5$ bacilli).

Group 6: young adult female outbred mice were vaccinated on day 0 into the scruff of the neck with BGC ($10^5$ bacilli) to which heat-killed *Mycobacterium vaccae* ($10^7$ bacilli) had been added.

Group 7: young adult female outbred mice were vaccinated on day 0 into the scruff of the neck with BGC ($10^5$ bacilli) to which heat-killed *Rhodococcus ruber* ($10^7$ bacilli) had been added.

Group 8: young adult female outbred mice were vaccinated on day 0 into the scruff of the neck with BCG ($10^5$ bacilli) to which heat-killed *Rhodoccocus ruber* ($10^6$ bacilli) had been added.

All mice in Groups 4-7 were foot pad tested for tuberculin immune response at day 30. Then at day 40 each group was divided so that half of each group received no further treatment and the second half of each group received an injection of *Rhodococcus ruber* ($10^7$ bacilli). At day 50 the tuberculin test on the foot pad was repeated.

The result of Example 1 are shown in Table 1.

TABLE 1

Modulation of a cellular immune response by *Rhodococcus ruber* (R.r.)

| Day | Tuberculin response (microns) at | | 24-48 difference |
|---|---|---|---|
| | 24 hours | 48 hours | |
| Group 1—control | | | |
| 10 | 6.9 ± 4.5 | 5.3 ± 3.7 | 1.6 |
| 30 | 5.9 ± 4.7 | 5.2 ± 4.5 | 0.7 |
| 50 M.v. | 13.1 ± 5.6 | 14.0 ± 5.2 | +0.9 |
| | $p < 0.01$ | $p < 0.001$ | |
| Group 2—BCG | | | |
| 10 | 16.8 ± 11.1 | 16.8 ± 5.5 | 0 |
| 30 | 31.1 ± 17.8 | 16.9 ± 9.1 | 14.2 <0.05 |
| 50 M.v. | 33.9 ± 12.3 | 19.2 ± 11.3 | 14.7 <0.02 |
| Group 3—BCG + M.v. | | | |
| 10 | 14.6 ± 8.3 | 9.9 ± 2.7 | 4.7 |
| 30 | 23.8 ± 16.1 | 21.7 ± 11.5 | 2.1 n.s |
| 50 M.v. | 27.4 ± 10.3 | 15.1 ± 5.8 | 12.3 <0.005 |
| Group 4—control | | | |
| 30 | 2.8 ± 3.7 | 2.5 ± 2.3 | 0.3 n.s. |
| 50 | 6.4 ± 9.4 | 3.6 ± 7.5 | 2.8 n.s. |
| 50 R.r. | 4.2 ± 5.4 | 1.0 ± 1.7 | 3.2 n.s. |
| Group 5—BCG | | | |
| 30 | 28.8 ± 15.4 | 19.1 ± 10.9 | 9.7 (<0.1) |
| 50 | 33.8 ± 21.6 | 12.0 ± 7.9 | 21.8 (<0.1) |
| 50 R.r. | 40.0 ± 22.4 | 12.2 ± 9.2 | 27.8 <0.05 |
| Group 6—BCG + M.v. | | | |
| 30 | 19.4 ± 20.5 | 17.7 ± 11.8 | 1.7 n.s. |
| 50 | 56.8 ± 53.8 | 29.4 ± 31.1 | 27.4 n.s. |
| 50 R.r. | 50.0 ± 38.4 | 9.0 ± 10.4 | 41.0 <0.05 |

TABLE 1-continued

Modulation of a cellular immune response by *Rhodococcus ruber* (R.r.)

| Day | Tuberculin response (microns) at 24 hours | 48 hours | 24-48 difference |
|---|---|---|---|
| Group 7—BCG + R.r. | | | |
| 30 | 20.6 ± 10.9 | 17.8 ± 10.3 | 2.8 n.s. |
| 50 | 24.8 ± 22.5 | 14.6 ± 13.2 | 10.2 n.s. |
| 50 R.r. | 28.0 ± 13.2 | 11.0 ± 4.7 | 17.0 <0.05 |
| Group 8—BCG + R.r./10 group | | | |
| 30 | 19.5 ± 13.9 | 20.9 ± 14.9 | +1.4 |
| 50 R.r. | 37.2 ± 25.2 | 20.2 ± 5.3 | 17.0 n.s. |
| 50 | 26.8 ± 14.8 | 12.8 ± 8.0 | 14.0 (<0.1) |

M.v. = *Mycobacterium vaccae*

In the control Group 1 *Mycobacterium vaccae* treatment induced a statistically significant increase in the immune response to tuberculin after both 24 hours (p<0.01) and 48 hours (p<0.001). However, in the control Group 4, treatment with *Rhodococcus ruber* did not induce a significant change in immune response to tuberculin after both 24 hours and 48 hours. At both time points the M.v. results were significantly greater than the R.r. results (p<0.02).

In the BCG groups (Group 2 and Group 5), the fall in response to tuberculin between 24 hours and 48 hours was greater (p=0.06) in the mice receiving treatment with *Rhodococcus ruber* (the mean fall being 28.2±15.7) than in the mice receiving treatment with *Mycobacterium vaccae* (the mean fall being 14.9±9.6).

In the BCG+*Mycobacterium vaccae* group (Group 3 and Group 6), the fall in response to tuberculin between 24 hours and 48 hours was again greater (p<0.05) in the group receiving treatment with *Rhodococcus ruber* (mean fall being 41.0±41.0) than in mice receiving treatment with *Mycobacterium vaccae* (mean fall being 12.7±7.0).

These data suggest that there is a down-regulation of the Th2 response after treatment with *Rhodococcus ruber*, which is not seen following treatment with *Mycobacterium vaccae*.

In the BCG+R.r. groups (Groups 7 and 8) the effect of adding R.r. $10^7$ (Group 7) or $10^6$ (Group 8) to BCG was very similar and after the second injection with R.r. there was a substantial reduction in response between 24 and 48 hours (15.5±10.0).

Example 2

Modulation of a Cellular Immune Response Using *Nocardia asteroides* (N.a), *Gordonia bronchialis* (G.b.) or *Tsukamurella inchonensis* (Tp.)

This experiment was designed to compare the effects of foot-pad testing with Tuberculin 28 days after vaccinating groups of 6 mice with BCG alone or with the addition of $10^7$ M.v., R.r., *Nocardia asteroides* (N.a.), *Gordonia bronchialis* (G.b.) or *Tsukamurella inchonensis* (T.p.). To find out what the effects were on the immune response to each of these added organisms, the groups of animals were tested in the other foot-pad 28 days after they had been tested with Tuberculin with skin-test reagents made from the organism included in their vaccination (Vaccin, Rubin, Asterin, Bronchialin and Inchonensin).

The results are detailed in Table 2.

TABLE 2

Modulation of a cellular immune response

| Day | Tuberculin response (microns) at 24 hours | 48 hours | 24-48 h difference |
|---|---|---|---|
| 1) Control group | | | |
| 28 | 3.8 ± 4.8 | 3.7 ± 3.6 | 0.1 |
| 2) BCG group | | | |
| 28 | 38.0 ± 20.2 | 28.2 ± 17.0 | 9.8 |
| Tuberculin | | | |
| 56 | 65.0 ± 31.2 | 45.8 ± 23.6 | 19.2 |
| 3) BCG + M.v. group | | | |
| 28 | 20.3 ± 10.0 | 14.2 ± 5.7 | 6.1 |
| Vaccin | | | |
| 56 | 18.7 ± 12.1 | 8.0 ± 6.5 | 10.7 |
| 4) BCG + R.r. group | | | |
| 28 | 31.3 ± 16.0 | 24.2 ± 10.3 | 7.1 |
| Rubin | | | |
| 56 | 19.5 ± 7.1 | 12.3 ± 10.4 | 7.2 |
| 5) BCG + N.a. group | | | |
| 28 | 24.2 ± 20.8 | 20.2 ± 17.6 | 4.0 |
| Asterin | | | |
| 56 | 7.3 ± 8.3 | 5.3 ± 5.0 | 2.0 |
| 6) BCG + G.b. group | | | |
| 28 | 15.8 ± 14.4 | 15.7 ± 13.2 | 0.1 |
| Bronchialin | | | |
| 56 | 11.3 ± 3.4 | 6.2 ± 4.3 | 5.1 |
| 7) BCG + T.p. group | | | |
| 28 | 19.5 ± 7.4 | 15.8 ± 5.7 | 3.7 |
| Paurometabolin | | | |
| 56 | 9.8 ± 5.0 | 2.3 ± 2.7 | 7.5 |

All of the bacterial suspensions depressed the 28 day Tuberculin response measured at both 24 and 48 hours, in comparison with that following BCG alone (p=0.05; p=0.2).

With the exception of Tuberculin and Vaccin, this was the first time that any of these skin test reagents have been used. The differences in responsiveness to the new reagents at 24 hours were probably because they had not been equilibrated except by protein estimation. However, all showed a fall in response between 24 and 48 hours at day 50, suggesting immunoregulatory activity.

Example 3

Modulation of a Cellular Immune Response by *Rhodococcus ruber* Treatment

This experiment was designed to investigate the effect of Diphtheria/Tetanus/Pertussis (DTP) vaccine and/or Measles/Mumps/Rubella (MMR) vaccine on subsequent BCG vaccination and how the effect can be modified by treatment with heat killed whole cells of *Rhodococcus ruber* given 7 days or 28 days in advance, or with the first dose of DTP.

The experimental design is detailed in Table 4. Groups of six weaning female outbred mice received the treatments detailed in Table 4. All mice were tuberculin-tested 28 days after BCG vaccination.

The results are presented in Table 3.

TABLE 3

| | Tuberculin response (microns) at | | |
|---|---|---|---|
| | 24 hours | 48 hours | 24-48 h difference |
| Group 5 in Table 4 | | | |
| BCG only: | 35.0 ± 24.7 | 22.0 ± 14.8 | 13.0 |
| Group 3 in Table 4 | | | |
| DTP/MMR then BCG: | 42.7 ± 28.5 | 24.2 ± 13.2 | 18.5 |
| Group 4 in Table 4 | | | |
| DTP/MMR then BCG: | 42.0 ± 21.1 | 23.7 ± 8.0 | 18.3 |
| Group 6 in Table 4 | | | |
| R.r. given 49 days before BCG: | 50.3 ± 47.0 | 31.8 ± 32.0 | 18.5 |
| Group 1 in Table 4 | | | |
| R.r. given 7 days before DTP/MMR then BGG: | 32.0 ± 18.4 | 24.3 ± 15.4 | 7.7 |
| Group 2 in Table 4 | | | |
| R.r. given 28 days before DTP/MMR then BCG: | 44.7 ± 25.8 | 20.0 ± 11.0 | 24.7 |
| Group 7 in Table 4 | | | |
| R.r. DTP/MMR then BCG: | 40.3 ± 26.0 | 27.3 ± 16.5 | 13.0 |

Trends Shown in this Experiment:

The effect of giving DTP/MMR before BCG (Groups 3 & 4 in Table 4): the administration of DTP and MMR before vaccination with BCG results in an increase in the 24 hour response and better separation between the 24 and 48 hour responses.

The effect of giving R.r. before BCG (Group 6 in Table 4): R.r. given 49 days before BCG increases the Tuberculin response at 24 and 48 hours, and increases the difference between them.

The effect of giving R.r. before DTP/MMR before BCG (Groups 1 & 2 in Table 4): giving R.r. 28 days before DTP/MMR increases the separation between the 24 and 48 hour Tuberculin responses, whereas giving R.r. 7 days before DTP/MMR suppresses the effect on subsequent BCG.

The effect of giving R.r. with the first dose of DTP/MMR before BCG (Group 7 in Table 4): giving R.r. with the first injection of DTP appeared to make no difference to the effect of DTP/MMR on subsequent BCG vaccination.

Preliminary findings suggest that immunization with DTP followed by MMR, prior to BCG vaccination, has an effect on Tuberculin reactivity 28 days later. The study also suggests that vaccination with R.r. prior to BCG vaccination, has an effect on Tuberculin reactivity 28 days later. The timing of vaccination with R.r. in relation to DTP/MMR prior to BCG vaccination may be important.

Example 4

Local Skin Reactions to Intradermal Injections in Adult Guinea Pigs

The left flank of 3 animals was shaved to give intradermal injections of 0.1 ml containing $10^8$ *M. vaccae* at the head end and 0.1 ml containing $10^9$ *M. vaccae* 5 cm towards the tail end of the animal.

Another 3 animals were shaved in the right flank and given intradermal injections of 0.1 ml containing $10^8$ *R. rhodochrous* at the head end and 0.1 ml containing $10^9$ *R. rhodochrous* 5 cm towards the tail end of the animal.

| | Diameters of induration in mm | | | | | |
|---|---|---|---|---|---|---|
| Groups | 48 h $10^8$ | 7 d $10^8$ | 14 d $10^8$ | 48 h $10^9$ | 7 d $10^9$ | 14 d $10^9$ |
| *M. vaccae* | 2 × 2 | — | — | 4 × 4 | 2 × 3 | — |
| *M. vaccae* | — | — | — | 2 × 2 | 2 × 2 | 1 × 1 |
| *M. vaccae* | — | — | — | 5 × 5 | 1 × 2 | — |
| *R. rhodochrous* | — | — | — | 1 × 1 | 2 × 2 | — |
| *R. rhodochrous* | — | — | — | 1 × 1 | 2 × 2 | — |
| *R. rhodochrous* | — | — | — | 2 × 1 | 4 × 3 | 1 × 2 |

In 3 guinea pigs, the local reactions to intradermal injections (the route of injection to be typically used in veterinary and medical practice) of $10^9$ *R. ruber* (a typical dose for human and animal use) were similar to reactions to the same dose of *M. vaccae* in another 3 guinea pigs. At 48 hours after injection, reactions to *R. ruber* were smaller (p<0.05) than those to *M. vaccae*. Thus, *R. ruber* may be even more pharmaceutically acceptable than *M. vaccae*. There are no local reactions to either preparation at the $10^8$ dose.

Example 5

Toxicity Following Subcutaneous Injection

No evidence of toxicity to subcutaneous doses was observed in 17 rats receiving 3 injections of *R. ruber* when they were aged 1 day, 14 days and 28 days (the last of these were given 7 days after challenge with *Trypanosoma cruzi* in expt. 6).

The responses to $10^9$ *R. ruber* at 48 hours were smaller than those to the same dose of *M. vaccae* (p<0.05). There were no differences at 7 days or 14 days. Many mice have received injections of various species of the bacteria of the present invention, without any evidence of toxicity.

Example 6

Modulation of Trypanosomiasis in Rats

Preparation of Animals
i) One day old male "l" rats were injected into the scruff of the neck with $10^7$ *Rhodococcus ruber* or *Rhodococcus coprophilus* in a volume of 0.1 ml via subcutaneous injection.
ii) After 14 days old, the male "l" rats were given a second subcutaneous injection with $10^7$ *R. ruber* in 0.1 ml on the left side.

iii) Animals were challenged with live *Trypanosoma cruzi* on day 21 via the subcutaneous route with $10^6$ trypomastigotes of the Tulahuén strain of *T. cruzi*. Infective blood trypomastigotes were maintained by serial passage in CBi mice.

iv) Bloodstream forms of *T. cruzi* were assessed under standardized conditions, by direct microscopic observation of 5 μl of heparinized tail venous blood, at 7 and 14 days post-infection (pi). Data are expressed as number of parasites/50 fields.

v) 7 days later an additional subcutaneous injection of $10^7$ *R. ruber* was administered in a volume of 0.1 ml on the right side.

Control animals only received the challenge with *T. cruzi*.

Another group of animals was left unchallenged for comparison purposes.

The results are presented in Table 5.

TABLE 5

Parasitemias (Data are expressed as number of parasites/50 fields)

| GROUP | n | Day 7 Mean ± SD | Day 7 Median (rank) | Day 14 Mean ± SD | Day 14 Median (R) |
|---|---|---|---|---|---|
| | | 1st Experiment | | | |
| Controls | 7 | 2.57 ± 1.8 | 2(1-5) | 1.14 ± 1.07 | 1(0-3) |
| Rr | 10 | 0.30 ± 0.67 | 0(0-2) | 0 ± 0 | 0(0-0) |
| | | P < 0.005 Student's t test | | P < 0.005 | |
| | | 2nd Experiment | | | |
| Controls | 7 | 2.14 ± 1.07 | 2(1-4) | 1 ± 1.15 | 1(0-3) |
| Rr | 7 | 1.1 ± 0.69 | 0(1-2) | 1.5 ± 0.97 | 2(0-3) |
| | | P = 0.05 Student's t test | | | |

| | | Pooled data from both experiments | | | |
|---|---|---|---|---|---|
| GROUP | n | Day 7 Mean ± SD | Day 7 Median (rank) | Day 14 | |
| Controls | 14 | 2.35 ± 1.44 | 2(1-5) | 1.07 ± 1.07 | 1(0-3) |
| Control 2 | 6 | 3.83 ± 4.36 | | 3.50 ± 2.89 | |
| Rr | 17 | 0.65 ± 0.78 | 0(1-2) | 0.69 ± 1.01 | 0(0-3) |
| Rc | 6 | 1.67 ± 0.81 | | 0.75 ± 1.5 | |
| | | P = 0.001 Student's t test | | | |

Rc = *Rhodococcus coprophilus*

This data, demonstrates a significant reduction of parasites circulating in the blood at the time when the greatest numbers are found in the control animals. This suggests that both *R. ruber* and *R. coprophilus* enhance the Th1 responses (7 days is too early for antibody production via the Th2 route).

Example 7

Investigating the Effects of *Rhodococcus coprophilus* NCIMB 11211, *Gordonia bronchialis* NC10667 and *Tsukamurella inchonensis* NC13040 on Toxicity, in Particular Growth Rate and Subsequent BCG Vaccination in Newborn Mice An alternative test of toxicity is that in which subcutaneous injections of Gordonia bronchialis, Rhodococcus coprophylus or *Tsukamurella inchonensis* are given on the day of birth, and again in a separate site, on day 21. These animals, and saline-injected controls were weighed at regular intervals over 3 months.

Methods 9 late term pregnant Balb C mice are used.

Preparation of killed bacterial suspension: Suspension prepared from 10 day Sauton antifoam broth culture, centrifuged and resuspended as a 10 mgs/ml in borate buffered saline, autoclaved and stored at 4° C. Dilute 10 mgs/ml, $10^{10}$/ml ½ in borate giving $5 \times 10^9$ and then diluting 1/10 in borate buffer giving a final concentration of $10^7$ in 20μ for use.

Day 1

On day of birth remove newborn mice singly and inject litter with $10^7$ killed suspension into the scruff and return to mother.

Inject control litters with 20 μliters of M15 borate buffered saline into the scruff.

Litter 1=2 female+3 male (Rhodococcus coprophilus NCIMB 11211)

Litter 2=2 female+3 male (Rhodococcus coprophilus NCIMB 11211)

Litter 3=5 female+3 male (*Gordonia bronchialis* NC10667)

Litter 4=3 female+4 male (*Gordonia bronchialis* NC10667)

Litter 5=1 female+1 male (Borate buffered saline)

Litter 6=3 female+1 male (Borate buffered saline)

Litter 7=5 female+3 male (Tsukamurella inchonensis NC13040)

Litter 8=5 female+4 male (Tsukamurella inchonensis NC13040)

Litter 9=4 female+5 male (borate buffered saline)

Day 21

Wean the mice, sex and separate the litters into 2 groups male and female

Weigh and revaccinate. Mark individuals by tail marking with an indelible pen.

Weigh and re tail mark weekly for 3 months.

FIG. 1 demonstrates the results of weight gain means/litter females test and controls over 12 weeks from weaning.

Figure 2:
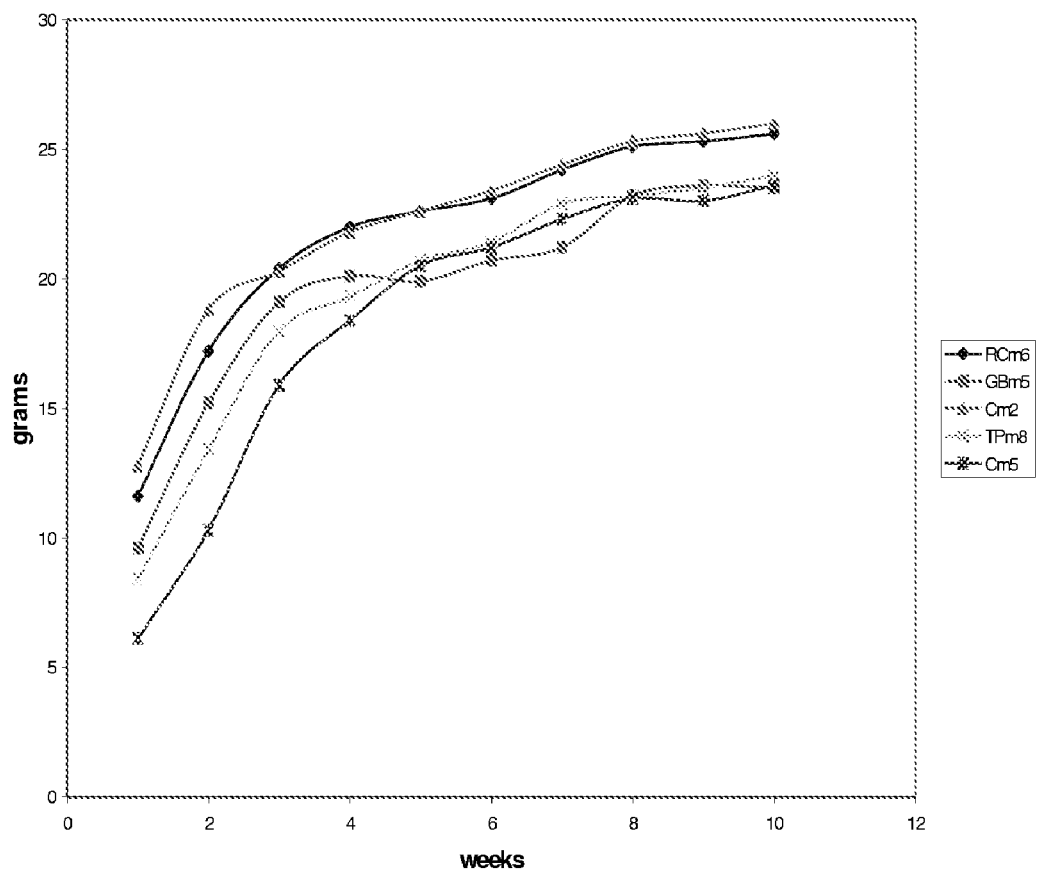
FIG. 2 is a graph demonstrating the results of weight gain mean/litter males test and controls over 12 weeks from weaning.

FIG. 2 demonstrates the results of weight gain mean/litter males test and controls over 12 weeks from weaning.

Weight gain is the same in all groups, and only 2/57 animals died over the 3 months. Both were males, that died just after being put together with other males after weaning. Thus it can be concluded that weight gain and progress of the animals was unaffected by the three species tested.

Example 8

The Effect on BCG Immunization Measured Through the Tuberculin Skin Test Response An immune modulator test model is devised, based upon the principle that vaccination with BCG induces a response to skin-testing with Tuberculin (a soluble preparation of tubercule bacilli), when tested 4 weeks later. The local reaction is measured 24 hours, 48 hours and 72 hours after injection of Tuberculin. In the mouse the reaction is usually largest at 24 hours when it is an indicator of the Th1 response to the antigens in Tuberculin. The reaction at 48 hours is usually less and includes a Th2 contribution. The reaction at 72 hours is often little less than at 48 hours and is a Th2 response. This post-BCG Tuberculin reaction can be modulated by prior priming, so that the Th1 and Th2 components of the reaction will reflect the nature of the priming reagent.

Methods

Mice primed according to Example 8 when 3 months old were injected with $10^6$ BCG in 100 µl into the scruff to half of each test and the control group.

At 4 months tuberculin test with reagent T1475 1 mg/ml. Dilute 100 µliters in 1.9 ml to give final concentration of 50 µgms/ml. Store at 4° C. Dose is 2.5 µg in 50 µliters given into the hind footpad. Tuberculin response swelling as measured using a micrometer at 24, 48 and 72 hours.

Results

Figure 3:
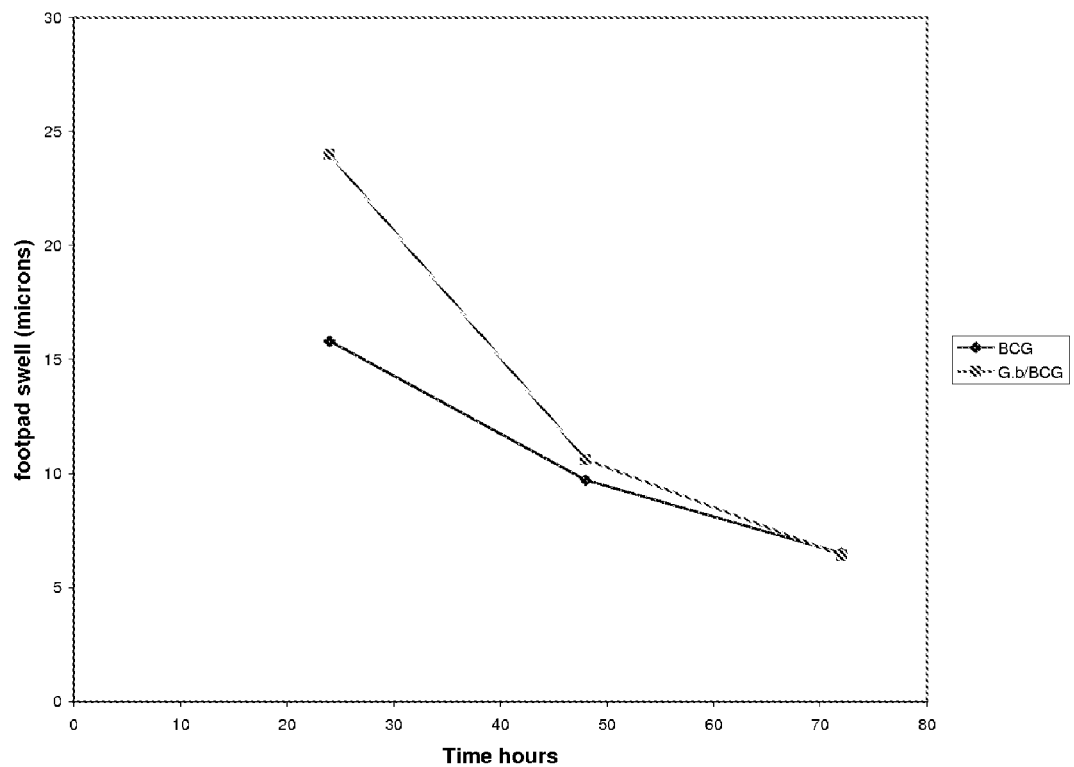
FIG. 3 is a graph demonstrating that *Gordonia bronchialis* enhances the early TH1 effect.

FIG. 3 shows that *Gordonia bronchialis* enhances the 24 hour TH1 effect.

Figure 4:
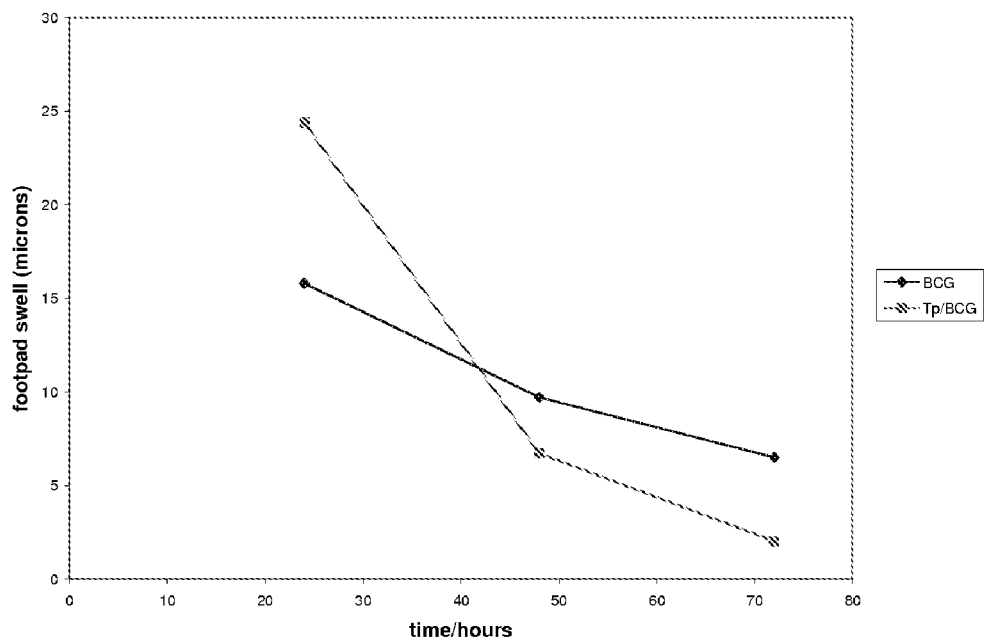
FIG. 4 is a graph demonstrating that *Tsukamurella inchonensis* enhances the early TH1 response and suppresses the late TH2 response.
Figure 5:
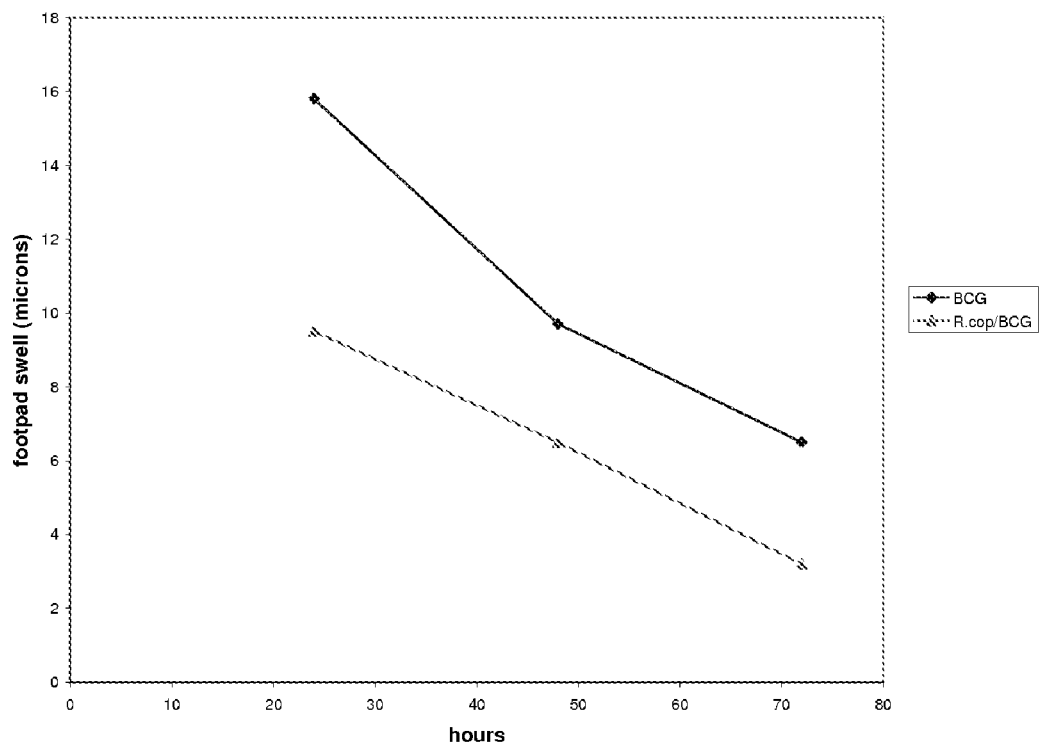
FIG. 5 is a graph demonstrating that *Rhodococcus coprophilus* suppresses both the TH1 and TH2 responses.

FIG. 4 shows that *Tsukamurella inchonensis* enhances the 24 hour TH1 response and suppresses the 72 hour TH2 response FIG. 5 shows that *Rhodococcus coprophilus* suppresses both the TH1 and TH2 responses

| | | Swelling (microns, means ± SD) | | |
|---|---|---|---|---|
| | | 24 hs | 48 hs | 72 hs |
| BCG alone | 6 | 9 ± 4.19 | 7.67 ± 3.39 | 3.7 ± 3.5 |
| Dietza maris | 4 | 13.25 ± 5.79 | 8.75 ± 3.95 | 5 ± 4.7 |
| G. terrae | 11 | 11.4 ± 5.09 | 9.9 ± 4.95 | 4.7 ± 4.08 |
| R. rhodococcus | 3 | 11.7 ± 6.4 | 6.3 ± 4 | 5 ± 2.6 |
| G. bronchialis | 4 | 10.5 ± 2.6 | 3.5 ± 1 | 1.25 ± 1.25 |
| G. amarae | 9 | 6.9 ± 3.7 | 4 ± 3.16 | 2 ± 1.9 |
| N. asteroides | 6 | 6.7 ± 3.98 | 2 ± 2.6 | 1 ± 2.6 |
| T. inchonensis | 4 | 6 ± 2.8 | 4 ± 2.83 | 2 ± 2.7 |
| R. rhodnii | 10 | 7 ± 4.87 | 7.9 ± 6.38 | 2.5 ± 2.8 |
| G. sputi | 8 | 4 ± 3.6 | 7.25 ± 5.6 | 2.12 ± 2.59 |
| R. coprophilus | 4 | 3 ± 1.4 | 0.75 ± 1.5 | 0.25 ± 0.5 |
| | | P < 0.0025 | P < 0.005 | P = 0.062 |

Conclusion

The species tested each induced different effects on the tuberculin test following BCG challenge:

*Rhodococcus rhodocrous* induced an enhanced Th1 response, without changing the Th2 response. It has also been shown that *Rhodococcus rhodnii*, *Dietzia maris* and *Gordonia terrae* also have this function. *Rhodococcus ruber* also has this function.

*Tsukamurella inchonensis* enhanced or left unchanged the Th1 response and down-regulated the Th2 response. It has also been shown that *Gordonia bronchialis*, Gordonia amarae and *Nocardia asteroids* also have this function.

*Rhodococcus coprophilus* strongly down-regulated both Th1 and Th2 responses.

These results also clearly show that the influence of 2 priming immunizations with any of the representative species of the invention persists for at least 9 weeks after the second immunization.

Example 9

Immune Modulator Test Model

An immune modulator test model is devised, based upon on the principle that vaccination with BCG induces a response to skin-testing with Tuberculin (a soluble preparation of tubercule bacilli), when tested 4 weeks later. The local reaction is measured 24 hours, 48 hours and 72 hours after injection of Tuberculin. The reaction is usually largest at 24 hours when it is an indicator of the Th1 response to the antigens in Tuberculin. The reaction at 48 hours is usually less and includes a Th2 contribution. The reaction at 72 hours is often little less than at 48 hours and is a Th2 response. This post-BCG Tuberculin reaction can be modulated by prior priming, so that the Th1 and Th2 components of the reaction will reflect the nature of the priming reagent.

The known immunostimulant, BCG is injected into the scruff of young 3 week old mice and the tuberculin response measured 1 month later by subcutaneous injection of tuberculin into the mouse footpad. The resultant swelling ie. the "tuberculin response" is then measured at 24, 48 and 72 hours. Swelling at 24 hours is considered an early or Th1 mediated response and swelling at 48 and 72 hours a late or Th2 mediated response. BCG in the healthy mouse stimulates predominantly a Th1 response.

Method (a) BCG Intradermal Vaccine 10 Dose Vial (Evans Medical).

Reconstitute with 1 ml supplied sterile water using a syringe and needle allowing 5 minutes to dissolve. Should be $1 \times 10^7$/ml.

Using a syringe and needle remove all of the vaccine and transfer to a plastic bijou bottle.

Dilute 1/10 0.15 ml in 1.35 ml M15 borate buffered saline gives $10^5$ in 100 µliters Dose is $10^5$ in 100 µl given into the scruff of the neck.

(b) Tuberculin

T1475 1 mg/ml.

Dilute 100 µl in 1.9 ml to give final concentration of 50 µgms/ml.

Store at 4° C.

Dose is 2.5 µg in 50 µl given intradermally into the hind footpad.

Tuberculin response is measured at 24, 48 and 72 hours using a micrometer

Figure 6:
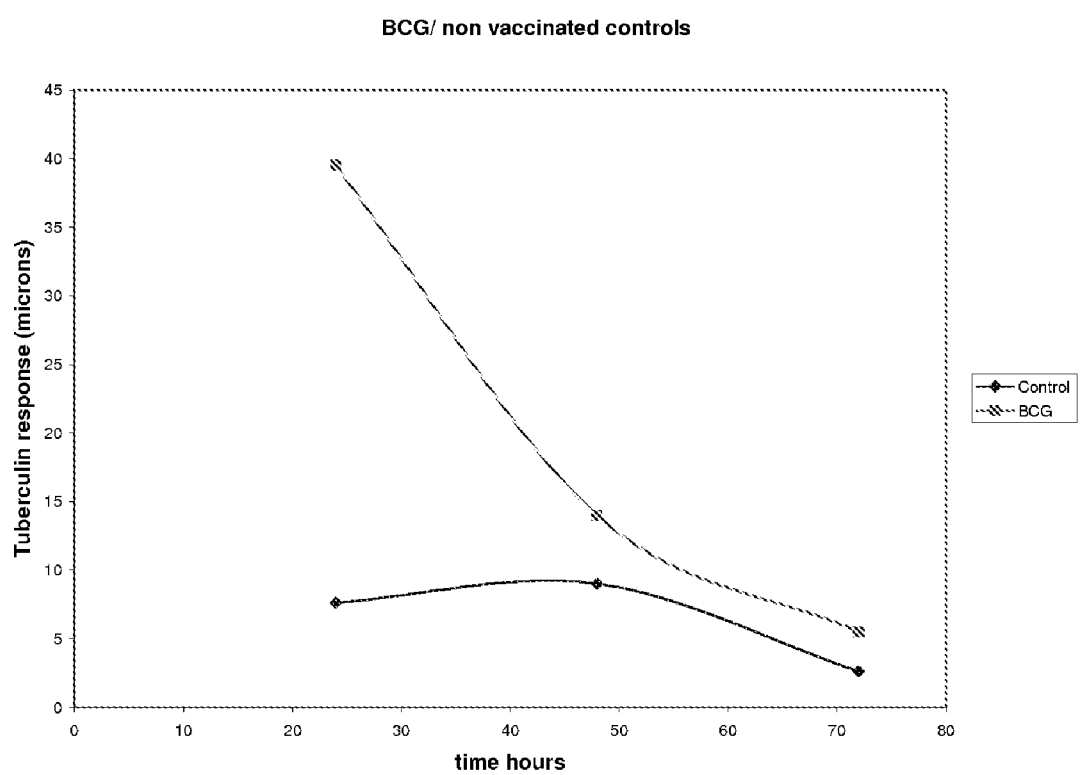
FIG. 6 is a graph demonstrating the tuberculin response to BCG after 1 month compared to non vaccinated controls.

FIG. 6 shows the tuberculin response to BCG after 1 month compared to non vaccinated controls.

(c) Preparation of Test Suspensions

Cultures are grown in Sauton broth harvested by centrifugation and resuspended at a concentration of 10 mg/ml in M15 borate buffered saline and stored at 4° C.

10 mgs/ml=$10^9$ in 100 µl.

Dilute 1/10=$10^8$ in 100 µl.

Add 150 µl $10^8$ to 1.2 ml M15 borate and add 15 µl BCG.

Dose is now $10^5$ BCG+$10^7$ test organism in 100 µl injected into the scruff of the neck.

Results

Figure 7:
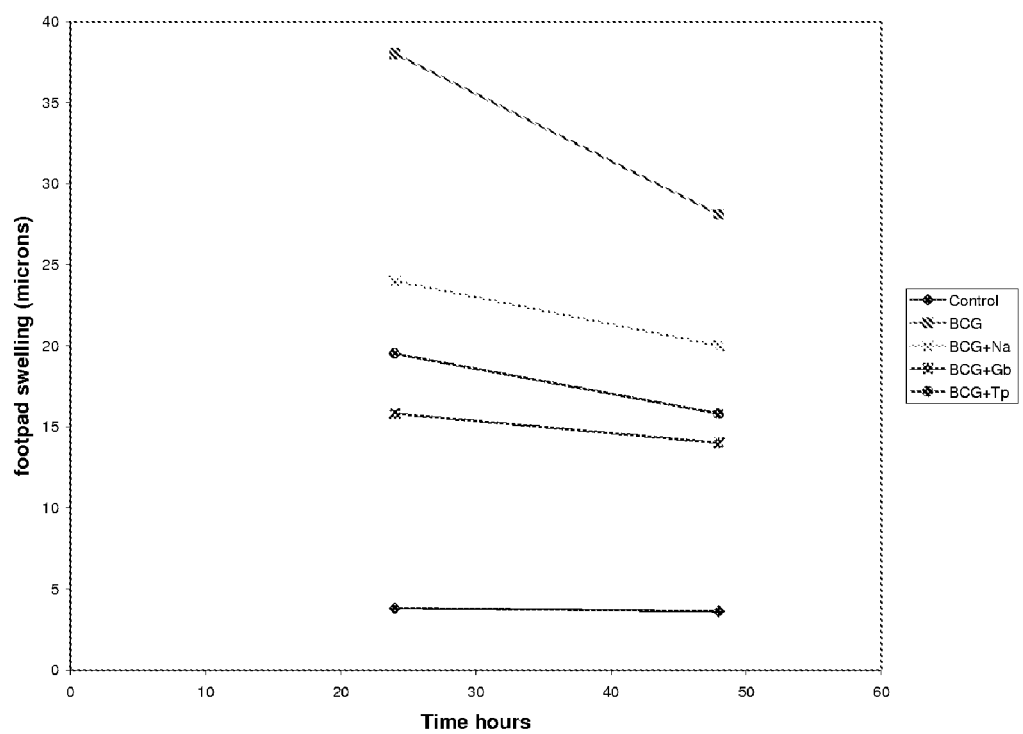
FIG. 7 is a graph demonstrating the immune modulation of the BCG effect by three species of bacteria. Tuberculin responses are measured at 24 and 48 hours. Representative species are (Na) *Nocardia asteroides*; (Gb) *Gordonia bronchialis*; and (Tp) *Tsukamurella inchonensis*.

FIG. 7 is a graph demonstrating the immune modulation of the BCG effect by three species of bacteria. Tuberculin responses are measured at 24 and 48 hours. Representative species are (Na) *Nocardia asteroids*; (Gb) *Gordonia bronchialis*; and (Tp) *Tsukamurella inchonensis*.

Figure 8:
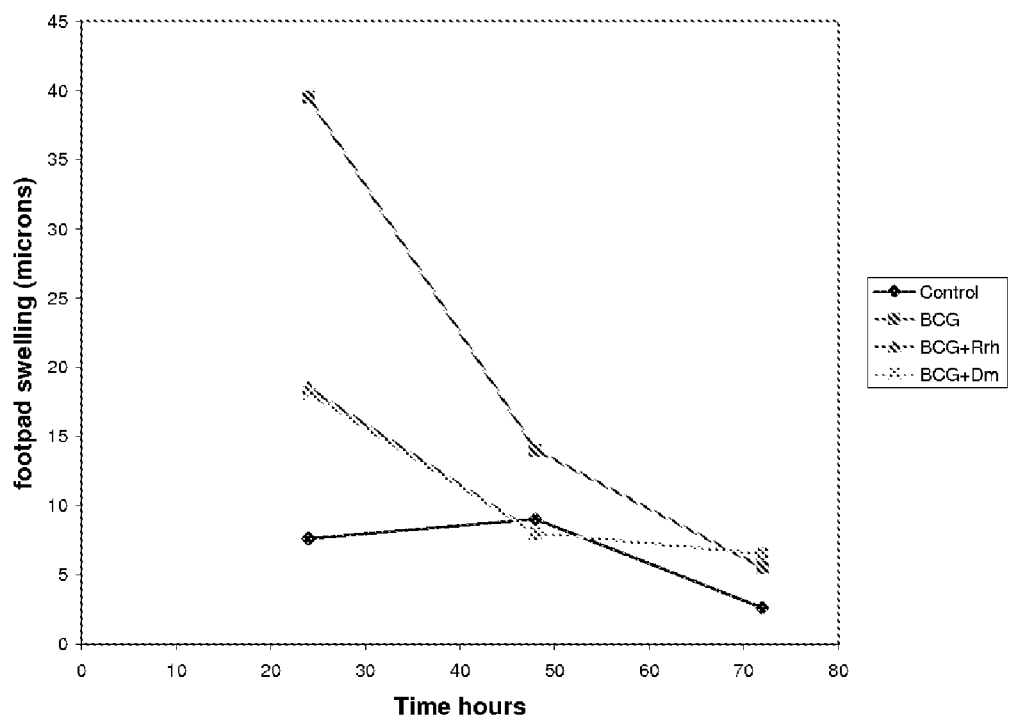
FIG. 8 is a graph demonstrating the immune modulation of BCG/BCG+ by two species of bacteria. Tuberculin responses are measured at 24, 48 and 72 hours. Representative species are (Rrh) *Rhodococcus rhodocrous* and (Dm) *Dietzia maris*.

FIG. 8 is a graph demonstrating the immune modulation of BCG/BCG+ by two species of bacteria. Tuberculin responses are measured at 24, 48 and 72 hours. Representative species are (Rrh) *Rhodococcus rhodocrous* and (Dm) *Dietzia maris*.

Figure 9:
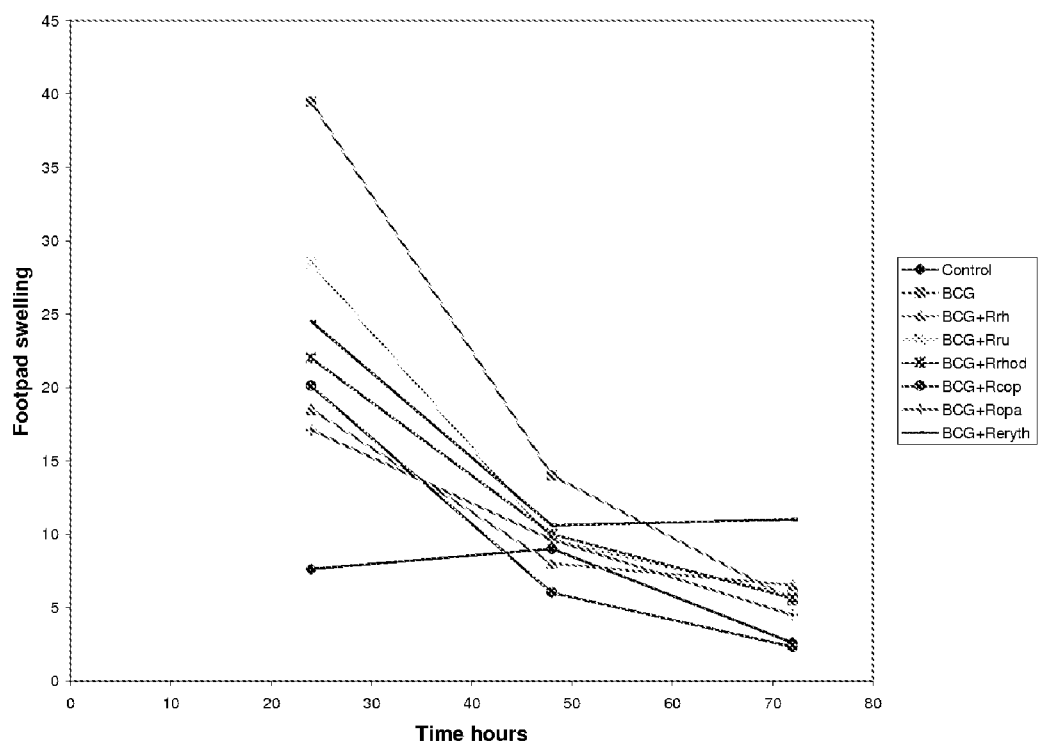
FIG. 9 is a graph demonstrating the immune modulation of the BCG effect by selected species within the genus *Rhodococcus*. Tuberculin responses are measured at 24, 48 and 72 hours. (Rrh) *Rhodococcus rhodocrous*; (Rru) *Rhodococcus ruber*; (Rrhod) *Rhodococcus rhodnii*; (Rcop) *Rhodococcus coprophilus*; (Ropa) *Rhodococcus opacus*; (Reryth) *Rhodococcus erythopolis*.

FIG. 9 is a graph demonstrating the immune modulation of the BCG effect by selected species within the genus *Rhodococcus*. Tuberculin responses are measured at 24, 48 and 72 hours. (Rrh) *Rhodococcus rhodocrous*; (Rru) *Rhodococcus ruber*; (Rrhod) *Rhodococcus rhodnii*; (Rcop) *Rhodococcus coprophilus*; (Ropa) *Rhodococcus opacus*; (Reryth) *Rhodococcus erythopolis*.

Figure 10:
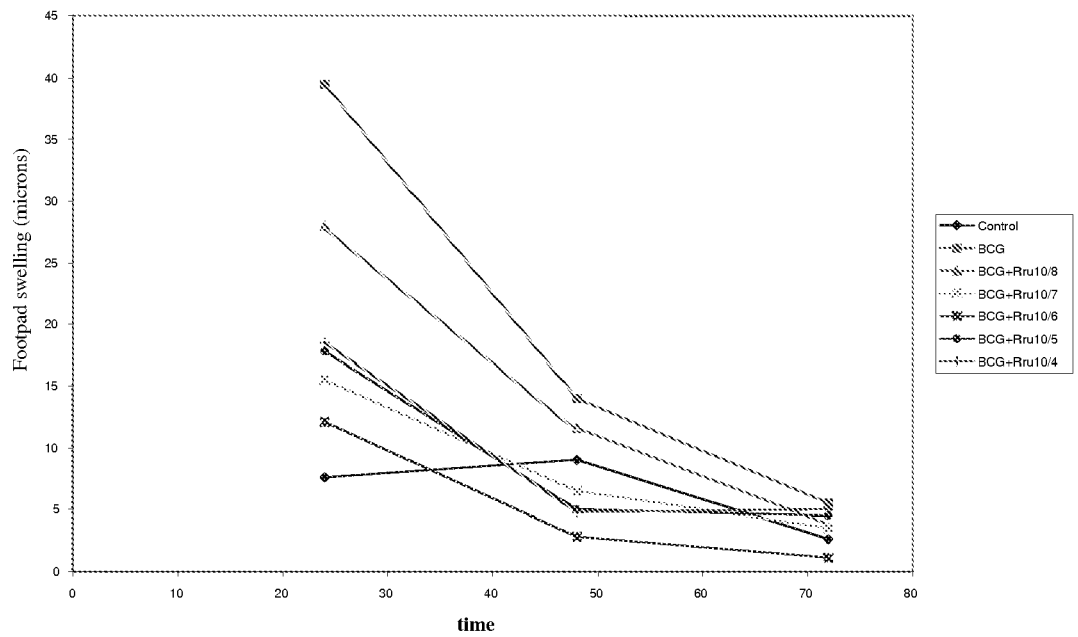
FIG. 10 is a graph demonstrating the optimal dose for *Rhodococcus ruber* using BCG modified with log dilutions of *Rhodococcus ruber* from $10^8$ to $10^4$ compared to BCG alone.

FIG. 10 is a graph demonstrating the optimal dose for *Rhodococcus ruber* using BCG modified with log dilutions of *Rhodococcus ruber* from $10^8$ to $10^4$ compared to BCG alone.

Conclusion

This screening test demonstrates that by mixing test suspensions with BCG and comparing to BCG alone, 28 days later the tuberculin test, as a measure of response to BCG, has been regulated or modified. In this simple model, immunoregulation is shown as a depression in the size of the response at both 24 and 48 hours. This can be further investigated in longer term experiments in which priming with the test suspension is carried out some weeks before challenge with BCG and subsequent Tuberculin testing.

Example 10

Growth Enhancement in Pigs

This is based on the principle that an immune system primed for Th1 enhancement, with or without regulation of Th2 results in less restriction of growth by subclinical infections. Thus in a situation where minor infections are frequent, a reduction of their influence should result in the animals putting on more weight. This might be achieved by reducing the level of circulating TNF (Tumour Necrosis Factor), which in the presence of Th2 cytokines acts as "cachectic factor", reducing appetite and increasing the metabolic rate.

The study was carried out in 10 newborn piglets. These animals were kept with all the others born that week.

On the day of birth: all piglets received intradermal injections of 0.1 ml over the left side of the neck. They were then weighed and returned to the sow. The control group (5 piglets) received injections of borate buffered (pH 8) saline as placebo. The test group (5 piglets) received 500 micrograms *Rhodococcus coprophilus* in 0.1 ml borate buffered (pH 8) saline.

On day 7: all piglets received intradermal injections of 0.1 ml over the right side of the neck. They were then weighed and returned to the sow. The control group received injections of borate buffered (pH 8) saline as placebo. The test group received 500 micrograms *Rhodococcus coprophilus* in 0.1 ml borate buffered (pH 8) saline On day 14: all piglets received intradermal injections of 0.1 ml over the right side of the neck. They were then weighed and returned to the sow. The control group received injections of borate buffered (pH 8) saline as placebo. The test group received 2 mg *Rhodococcus coprophilus* in 0.2 ml borate buffered (pH 8) saline The data is presented hereinbelow:

| Groups | Weeks | | | | | | |
|---|---|---|---|---|---|---|---|
| | 0 | 1 | 2 | 5 | 8 | 9 | 11 |
| Placebo (Pl) (kg) | 1.46 | 3 | 4.68 | 9 | 16.62 | 19.76 | 28.06 |
| Rhodo (Ro) (kg) | 1.76 | 3.26 | 5.2 | 10 | 20.24 | 22.36 | 33.1 |

Figure 11:
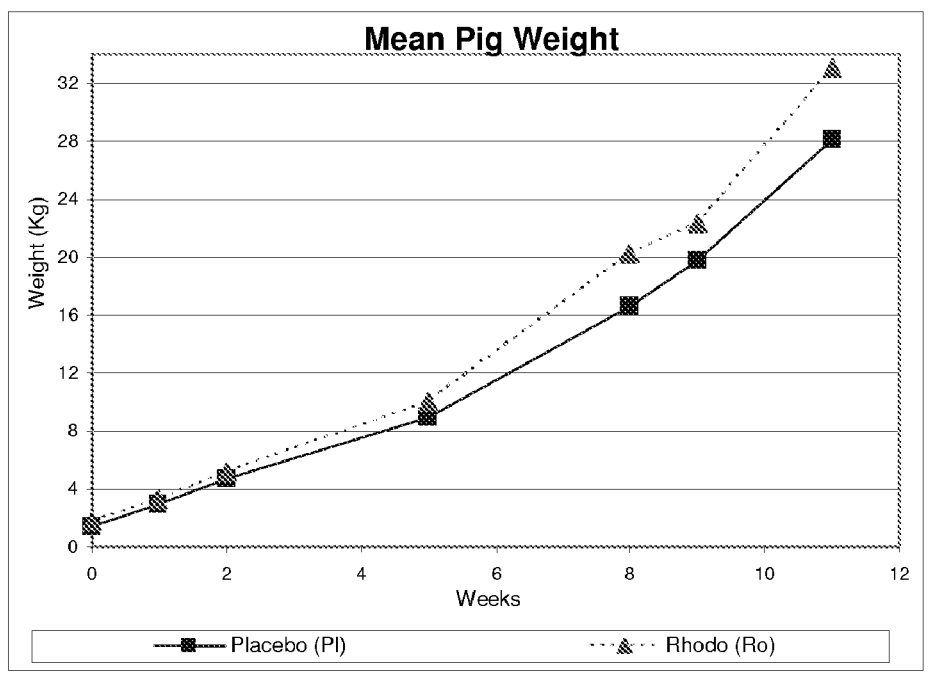
FIG. 11 is a graph which shows the growth enhancement of pigs administered with *Rhodococcus coprophilus* (Ro) as test reagent.
Figure 12:
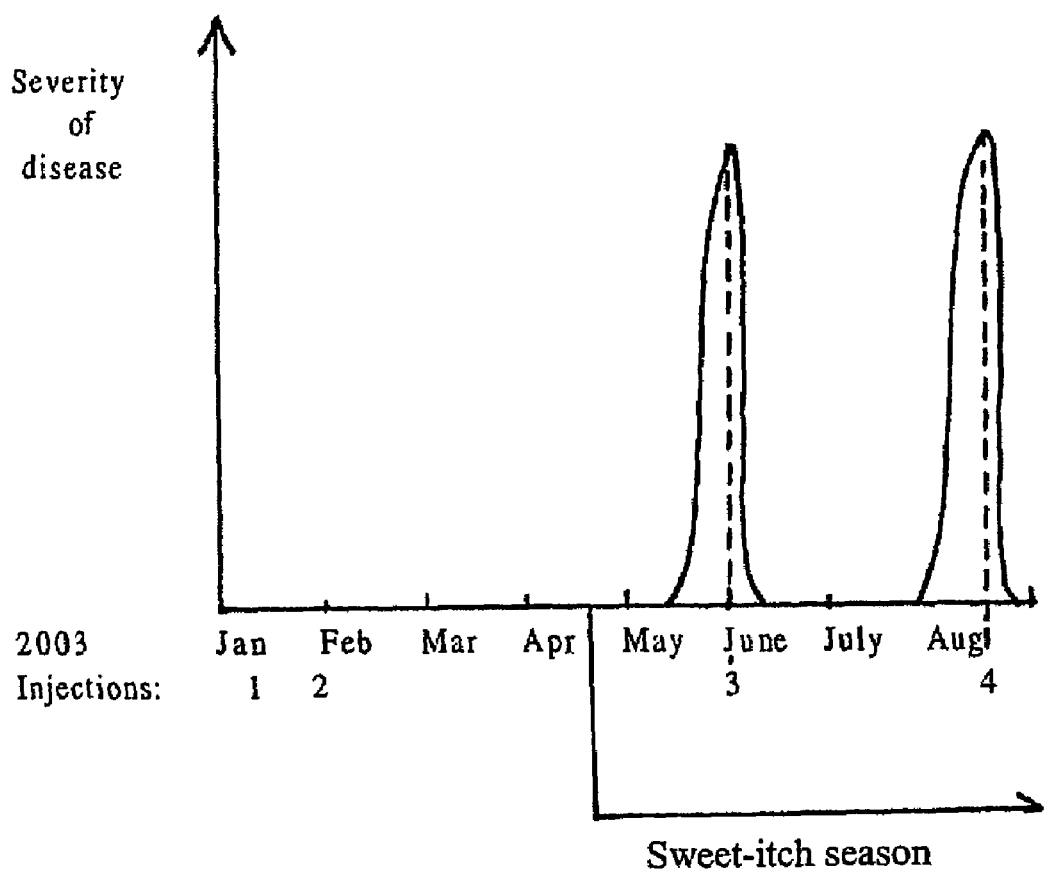
FIG. 12 shows the disease development of sweet-itch in a horse which is administered *T. inchonensis*.

In FIG. 11 a graph is shown which demonstrates the growth enhancement of pigs administered with *Rhodococcus coprophilus* (Ro) as test reagent.

Preliminary investigations show that piglets receiving *Rhodococcus coprophilus* put on significantly more weight than placebo controls given similar injections, but of buffered saline. The advantages of this may be that the pigs would reach regular slaughter weight (between 90-100 kg) 2 to 3 weeks earlier than usual.

Without wishing to be bound by theory it is surmised that the increased weight gain seen in animals receiving the test reagent may be due to one or more of the following: better food conversion, a reduction in infection and reduced stress.

Example 11

Modulation of Stress Associated with Sweet-Itch in Horses

Sweet-itch is the skin condition commonly troubling horses and ponies making an allergic response to bites by *Culicoides* midges. This most commonly occurs in areas where hair is long, such as the mane and tail. There is a loss of hair and thickening and inflammation of the skin with intense itching. Horses are excited and distressed by this condition and may lose weight as a result thereof. This is an annual condition affecting afflicted horses and ponies in the late spring and summer usually.

Groups of 4 ponies and horses known to develop sweet-itch every year, received *T. inchonensis* 1 mg by intradermal injection on 2 occasions 2-weeks apart, 4 animals received injections of buffered saline as a control, and 2 animals received 1 mg injections of *M. vaccae* as a positive control. Since this was being done during the sweet-itch season, animals wore a blanket, hood or mask to protect them from midge bites, which will be removed 3-weeks after the second injection. Following removal of the coats, sweet-itch is expected to occur within 1-2 weeks in the control group when the first full assessment of efficacy will be made. A third injection of the reagents may be given at that time.

The results are presented below:

| 1 | 3 | 15 | 16 | 12 | 17 | 2 | 5 | 6 | 7 | Horse |
|---|---|---|---|---|---|---|---|---|---|---|
| P | P | P | P | V | V | T | T | T | T | Reagent |
| B | B | B | B | B | B | B | B | B | B | Blanket |
| H | H | | H | | H | H | H | H | | Hood |
| | | | | | | | | | M | Mask |
| 5 | 4 | 5 | 5 | 5 | 5 | 4 | 4 | 3 | 5 | Tail Swishing 1-5 Constant |
| 0 | 2 | 53 | 1 | 5 | 0 | 1 | 0 | 5 | 11 | Head Shaking × 15 mins |
| 0 | 7 | 4 | 10 | 0 | 11 | 1 | 19 | 3 | 2 | Kicking at belly |
| 0 | 3 | 0 | 6 | 0 | 0 | 0 | 0 | 0 | 0 | Foot stamping |
| 0 | 4 | 8 | 7 | 0 | 3 | 0 | 1 | 1 | 1 | Rubbing |
| 0 | 3 | 0 | 2 | 0 | 3 | 0 | 1 | 1 | 2 | Biting |
| 0 | 0 | 2 | 3 | 0 | 0 | 0 | 0 | 2 | 1 | Mindless walking |
| 0 | 0 | 1 | 1 | 0 | 1 | 0 | 0 | 0 | 0 | Rolling |
| 1 | 2 | 4 | 6 | 1 | 5 | 1 | 5 | 2 | 6 | Observer impression 1-10 high |
| 6 | 25 | 77 | 41 | 11 | 28 | 7 | 30 | 17 | 28 | Total Score |
| P 37 | | | | V 19 | | T 21 | | | | Mean/Group |

The results show that both *M. vaccae* and *T. inchonensis* reduced the symptoms of stress caused by sweet-itch ($p<0.01$).

Example 12

Prevention of Sweet-Itch in Horses

A 7-year old horse known to regularly develop quite severe sweet-itch every year in the midge season, was given two intradermal injections of *T. inchonensis* in the front of the chest in January and February respectively with two weeks between the injections. Until the last few days of May and well into the *Culicoides* season the horse surprisingly showed no signs of sweet-itch, such as hair loss or skin inflammation. At the end of May sweet-itch did appear in the animal and a third injection of *T. inchonensis* was administered to the animal. Within 24-48 hours of administration the sweet-itch symptoms (in particular skin inflammation and/or hair loss) had completely disappeared. The animal was then again sweet-itch free until early August. Again a further (4$^{th}$) injection of *T. inchonensis* was administered and again the sweet-itch symptoms disappeared within 24-48 hrs post administration.

Figure 21:
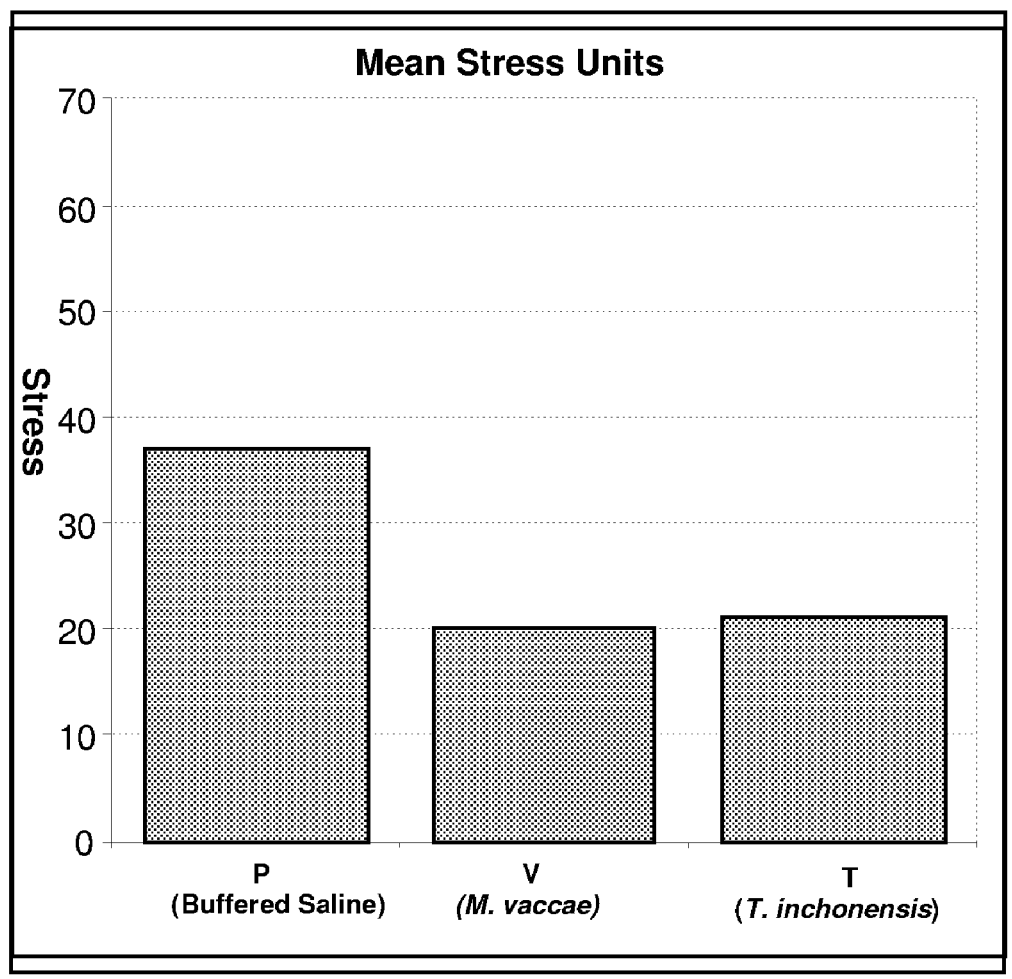
FIG. 21 shows a graphical representation of the stress response associated with sweet-itch in horses.

This data is presented in graphical form in FIG. 21.

The results show that *T. inchonensis* administered twice prior to the sweet-itch season and then again on an ad hoc basis during the sweet-itch season as and when the symptoms of sweet-itch occur will provide an effective prevention and/or treatment against sweet-itch.

Example 13

Cancer Model

This study assesses the effect of injections of $10^6$ and $10^7$ *Gordonia bronchialis*, *Rhodococcus coprophilus* and *Tsukamurella inchonensis* in the prevention and treatment of mice challenged with a lung adenocarcinoma cell line. Groups of mice will receive subcutaneous injections of the test species or saline placebo into the scruff of the neck 5 weeks and two weeks before subcutaneous challenge with tumour cells into the side. The third injection of the test organisms and saline placebo will be given into the scruff of the neck 1 week after tumour challenge. The number of tumour cells injected will be decided by those fully conversant with the system. End points will be the presence and size of the tumours at the challenge site 7, 14 and 21 days after challenge.

Preliminary investigations suggest that at least one of the test bacteria will delay tumour development and reduce tumour progression.

Example 14

To Show that the Suspensions of Whole Cells of the Bacteria are More Effective in Modulating Immunity than Cell Extracts, Comparative Preparations are Made and Tested in a BCG Challenge/Tuberculin Skin Test System 100 mg of *Tsukamurella inchonensis* are suspended in buffered saline (pH8.0) in a pre-weighed centrifuge tube at a concentration of 10 mg wet weight of organisms/ml. The entire 10 ml is treated in an ultrasonicator to break open the majority of organisms (70-80%).

The sonicate is centrifuged at 15000 rpm for an hour in a tube and the supernatant is carefully removed and passed through a 0.2 μm pore-size membrane filter as the test extract. The tube, with deposit, is weighed again to determine the proportion of whole organisms that are not broken open plus cell wall debris etc. This is 64 mg. The volume of extract equivalent to 0.01 mg *T. inchonensis* is then estimated and this is being compared with the equivalent 0.01 mg (approximating to 107) whole bacilli.

Groups of 10 animals are receiving injections of the extract or bacillary whole cell suspensions (equivalent to 0.01 mg/dose) or buffered saline placebo into the scruff of the neck at weaning and 7 days later. Two weeks later animals are challenged with BCG. 28 days later Tuberculin testing is performed with readings taken at 24, 48 and 72 hours. (This Data Will be Ready by September.)

Results:

Tuberculin responses in mice following BCG vaccination given after priming with nothing, borate buffer, *T. inchonensis* whole cells or soluble antigens (filtered sonicate).

Tuberculin response (microns) following BCG given to non-primed animals:—

| No. | 24 hours | 48 hours | 72 hours |
|---|---|---|---|
| 6 | 9 ± 4.2 | 7.7 ± 3.39 | 3.67 ± 3.5 |

Tuberculin response (microns) following BCG given to animals primed with borate buffer alone:—

| | | | |
|---|---|---|---|
| 6 | 9 ± 5.7 | 6.3 ± 7.1 | 3.17 ± 2.93 |

Priming with borate buffer has no effect on post-BCG Tuberculin test.

Tuberculin response (microns) following BCG given to animals primed with whole heat-killed *T. inchonensis*:—

| | | | |
|---|---|---|---|
| 6 | 7.3 ± 1.03 | 6.17 ± 3.87 | 1.5 ± 2.07 |

Priming with whole *T. inchonensis* decreases Tuberculin responses, notably at 72 hours (Th2 responsiveness).

Tuberculin response (microns) following BCG given to animals primed with *T. inchonensis* soluble preparation (filtered sonicate):—

| | | | |
|---|---|---|---|
| 6 | 6.8 ± 6.8 | 11.0 ± 8.0 | 4.6 ± 6.8 |

Priming with *T. inchonensis* filtered sonicate increases responses at 48 hours and 72 hours (Th2 responsiveness). This is probably due to an increase in inflammatory antibody production to shared antigens between BCG and *T. inchonensis*. The results show that priming with sonicate results in a response which is different from that following priming with whole killed organisms.

Preliminary investigations suggest that whole cells of the bacteria are more effective in modulating immunity than cell extracts.

Example 15

Stress in Pigs

To evaluate the effect of whole cells of bacteria from one or more of the genera *Rhodococcus*, *Gordonia*, *Nocardia*, *Dietzia*, *Tsukamurella* and *Nocardioides* on stress in pigs (piglets), one or more species from one or more of these genera were tested in pigs.

Measurement of salivary cortisol is a non-invasive method of quantifying acute stress in laboratory, farm, wild captive and free-living animals. We detail below a method of saliva collection from pigs or sheep and the use of a commercially available cortisol enzyme-linked immunosorbent assay (ELISA) designed to measure cortisol in human saliva. This ELISA kit has successfully been used to measure salivary cortisol in pigs and sheep.

Method

Collection of Saliva Samples.
1. Pigs have a strong circadian (daily) cortisol rhythm which means that they naturally have higher levels of stress hormones in the morning than later on in the day. In pigs, the highest cortisol levels are found at 0700 h and decrease toward midday. For this reason it is vital that saliva samples are always taken at the same time of day.
2. Feeding and drinking can affect the concentration of hormones in saliva. To obtain the most realistic results, take saliva samples when the pigs are not feeding or drinking. It is best to take samples before they feed or drink.
3. For small pigs, get the pig to chew on standard cotton wool buds (coloured ones are easier to find in hay) while you hold the other end. Approximately four cotton buds (both ends) should collect enough saliva for each pig. For larger pigs use the large cotton wool buds to collect saliva from the inside cheek. Approximately two large cotton buds should collect enough saliva. A minimum of 0.2 ml saliva is needed per pig.
4. Immediately after collection, cut the cotton bud to fit inside an ependorf micro-centrifuge tube. Place the cotton bud in the ependorf with the cotton bit at the top. Centrifuge at top speed for approximately two minutes or until the saliva has settled at the bottom of the ependorf. Flick the top of the bud to obtain the remaining saliva from the hollow part.
5. A minimum of 0.1 ml (first mark on ependorf) of saliva should be collected in each ependorf by centrifuging more than one cotton bud per ependorf, but one at time. Collect two ependorfs per pig.
6. Clearly mark the ependorf with identity numbers and the date.
7. As soon as possible store saliva samples in air-tight re-sealable bags in the freezer, preferably at −20° C.

Cortisol Assay.
1. Draw up a plate plan.
2. Remove saliva samples from the freezer and allow to defrost.
3. Switch the oven on at 25° C.
4. Bring ELISA reagents to room temperature before use.
5. Dilute wash solution following manufacturers instructions.
6. Dispense 100 µl of cortisol standards and saliva samples in duplicate into appropriate wells.
7. Dispense 200 µl of enzyme conjugate to each well.
8. Shake the plate for 10 sec.
9. Incubate at 25° C. (in oven) for 1 hr.
10. Wash all wells three times by disposing of the contents down the sink, dispense 400 µl wash solution into each well using the multichannel pipette, dispose of the contents again and repeat a further two times.
11. Tap the inverted plate onto absorbent towels firmly to remove any excess wash solution. The wash stage of the assay is very important, and the plate must be washed properly.
12. Dispense 200 µl of substrate solution to each well.
13. Incubate at 25° C. (in oven) for 30 min.
14. Without emptying the wells, dispense 100 µl stop solution to each well.
15. Read the plate at 450 nm within 10 min of adding the stop solution.

Salivary Cortisol ELISA Kit.
Kit of 96 wells for human saliva, available from:
Immunodiagnostic Systems Ltd,
10 Didcot Way,
Boldon Business Park,
Boldon,
Tyne and Wear,
NE35 9PD.

One or more saliva swabs will be taken from each animal at 3 weeks, at 64 days and at marketing aged 4-5 months. The saliva will be analysed for stress-related hormones, in particular cortisol.

It is expected that one or more of the test bacteria will reduce stress by neuro-endocrino-immunological mechanisms.

Example 16

Treatment of Equine Sarcoid

Equine sarcoid, the commonest skin neoplasm of horses, is associated with infection with bovine papilloma viruses 1 and 2.

A six-year old gelding (¾ thoroughbred; ¼ Belgian warmblood) had developed a number of sarcoid lesions over the preceding year or more. In Spring 2002 several small wart-like growths were found high in the groin/inner thigh area.

In August 2002—one tumour was near the sheath and when a photograph was taken this lesion was a grape-like cluster of growths about 3 cm in diameter, which has started to ulcerate. Part of this cluster was pedunculated, but was not suitable for ligation. Another group of non-ulcerated, wart-like growths had developed at the top of the right foreleg covering an area of about 3.5×2.5 cm. Twice-daily treatment with Camrosa ointment (herbal remedy) was started.

Figure 15:
FIG. 15 shows a photograph taken in August 2002 showing a sarcoid lesion prior to administering *T. inchonensis*.
Figure 17:
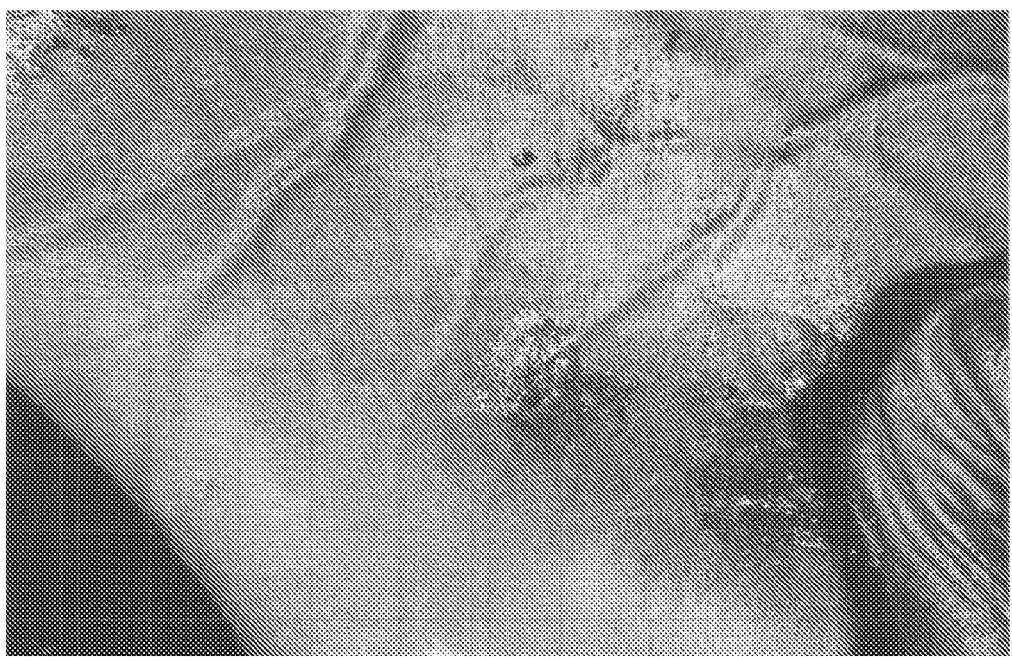
FIG. 17 shows a photograph taken in August 2002 showing a sarcoid lesion prior to administering *T. inchonensis*.

Photographs taken in August 2002 are shown in FIGS. 15 and 17.

In Autumn 2002, the small sarcoids remained unchanged but the group at the top of the foreleg continued to enlarge to cover an area of about 4.3×3 cm and the ulcerating growth near the sheath tripled in size.

January 2003—the first injection of *Tsukamurelia inchonensis* was given and the Camrosa ointment was continued twice a day as before. A very gradual reduction in size of all growths was noted during the next few months.

Initially, two intradermal injections of 1 mg *Tsukamurella inchonensis* were given two weeks apart some 8-10 cm from the chest lesion (i.e. the lesion as the top of the right foreleg) and in the same lymph node drainage area. Four weeks after the second injection, the chest lesion was flatter and resolving. The large penile lesion (i.e. the lesion near the sheath) was more obviously pedunculated and appeared to becoming necrotic.

A month after the second injection, a third injection of *T. inchonensis* was given, this time on the left front of the chest in a lymph node drainage area where there were no sarcoid lesions. A month later no further resolution of the sarcoids was observed.

A month after the third injection, a fourth was given, this time again within a few cm of the lesion on the right chest. A month after that the chest lesion had almost completely resolved, necrosis of the penile lesion was progressing and the other groin lesions were appreciably smaller.

In May 2003 application of Camrosa ointment was stopped for all but the ulcerated growth on which it was continued once daily as a fly repellant.

Figure 13:
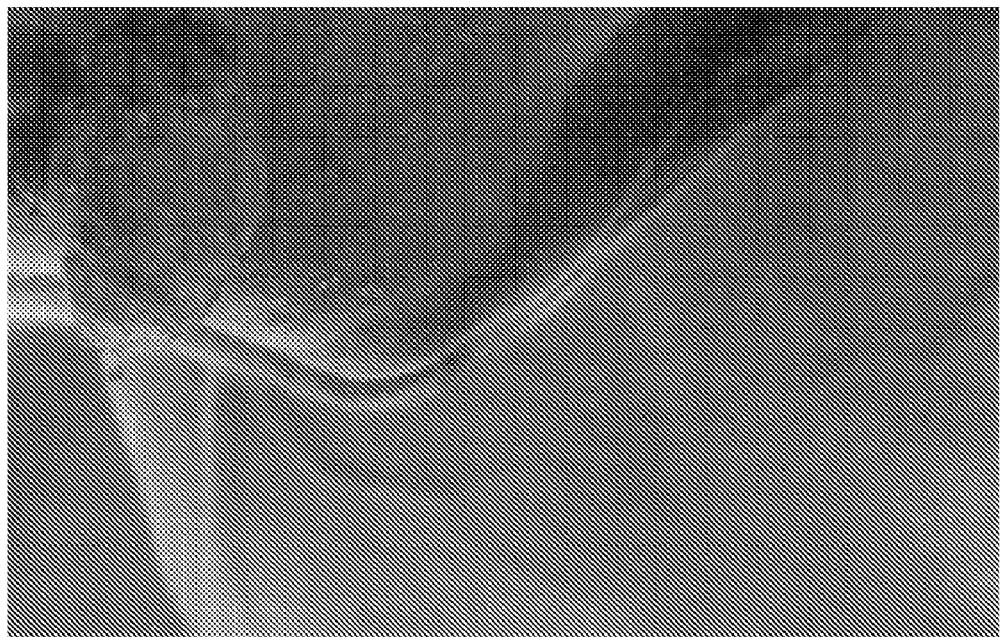
FIG. 13 shows a photograph taken in June 2003 showing a sarcoid lesion in horses administered with *T. inchonensis*.
Figure 14:
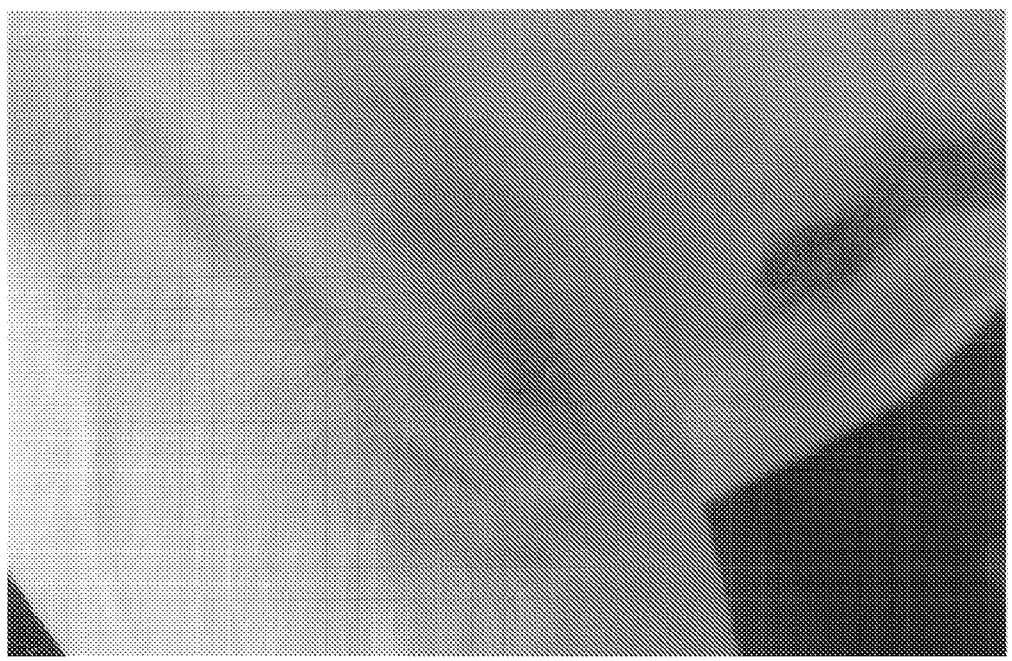
FIG. 14 shows a photograph taken in June 2003 showing a sarcoid lesion in horses administered with *T. inchonensis*.
Figure 16:
FIG. 16 shows a photograph taken in June 2003 showing a sarcoid lesion in horses administered with *T. inchonensis*.

Photographs taken in June 2003 are presented as FIGS. 13, 14 and 16.

By August 2003 all but one of the small growths had disappeared as had the group at the top of the foreleg. The growth near the sheath was still ulcerated but now about ¼ of its maximum size and small pieces of tissue flake off when the growth is cleaned.

Figure 18:
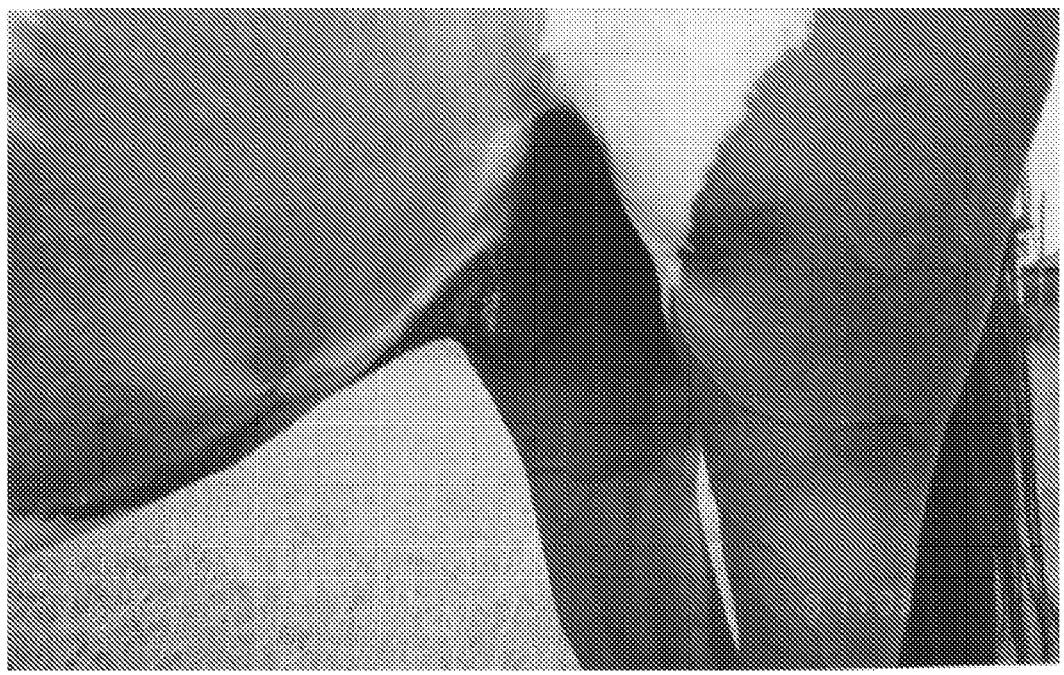
FIG. 18 shows a photograph taken in August 2003 showing a sarcoid lesion following administration of *T. inchonensis*. The lesion was much reduced (about a quarter of its maximum size [no photo]).
Figure 19:
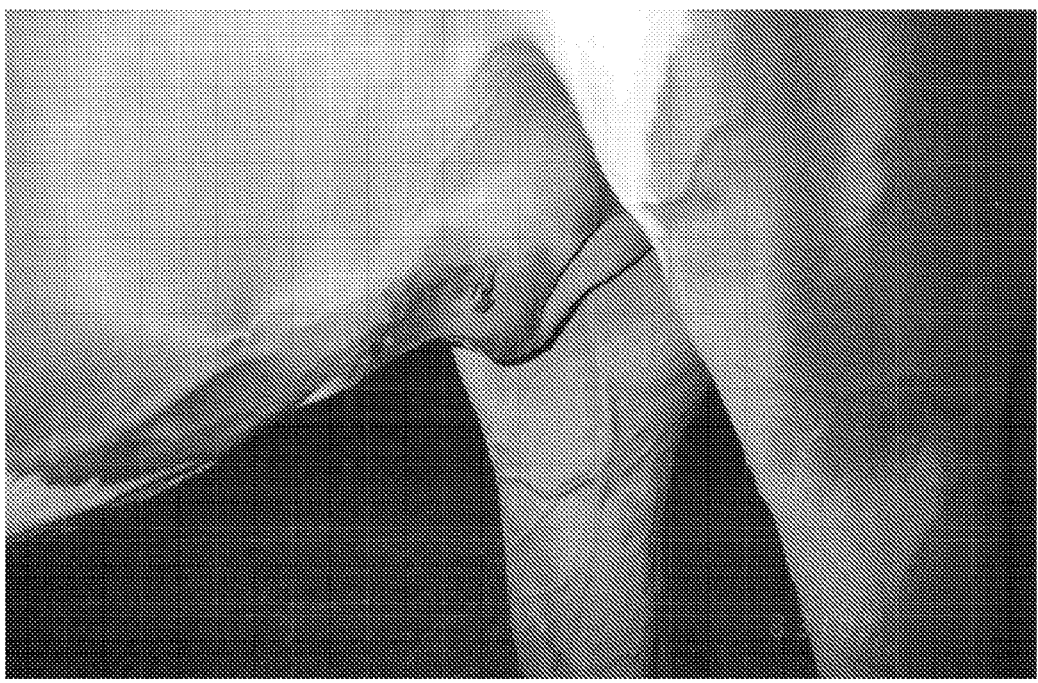
FIG. 19 shows a photograph taken in August 2003 showing a sarcoid lesion following administration of *T. inchonensis*. The lesion was much reduced (about a quarter of its maximum size [no photo]).
Figure 20:
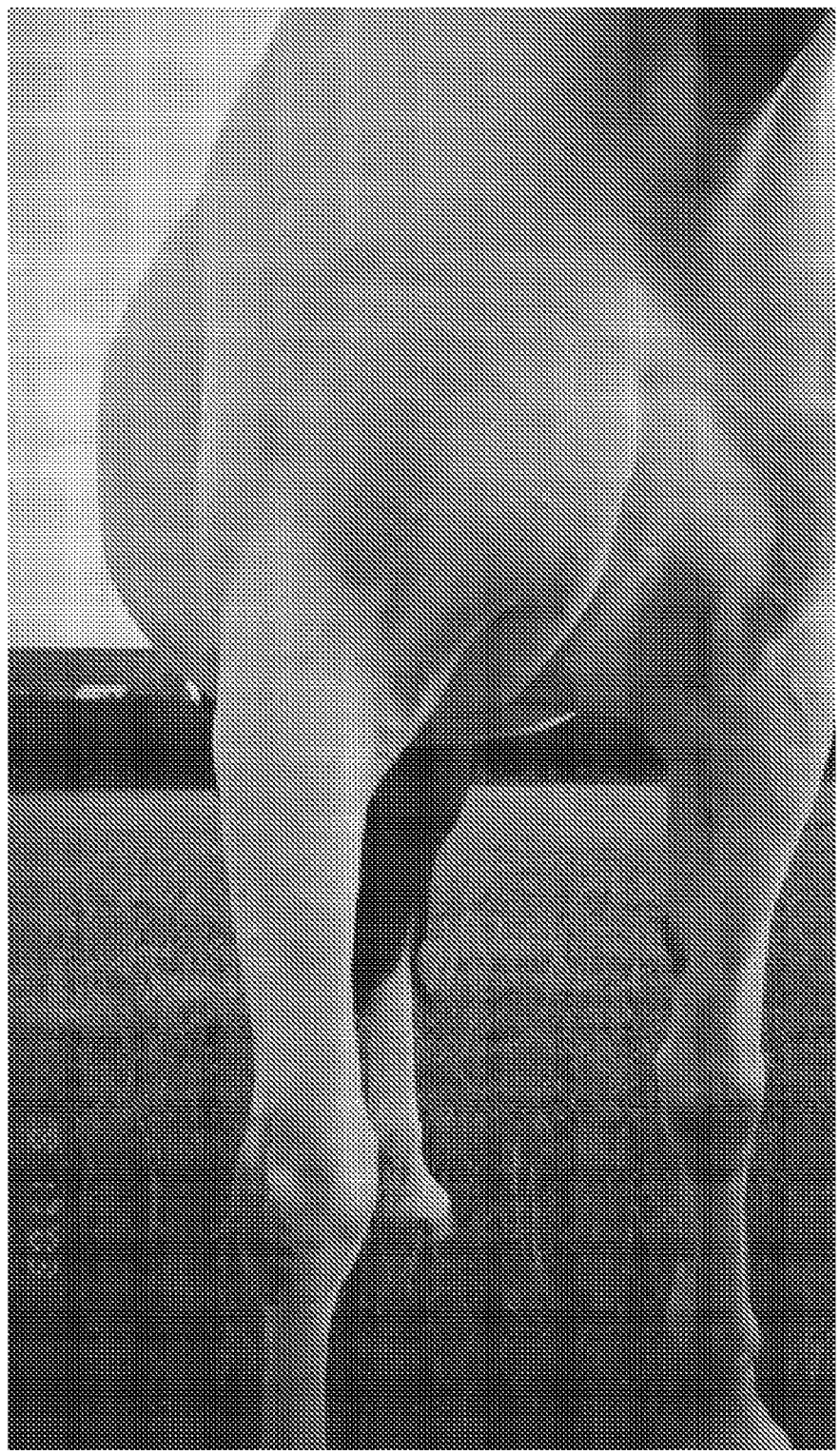
FIG. 20 shows a photograph taken in August 2003 showing a sarcoid lesion following administration of *T. inchonensis*.

Photographs taken in August 2003 are presented as FIGS. 18, 19 and 20. It is noted that the sarcoids shown in FIG. 17 had completely healed by August 2003 following administration of *T. inchonensis*.

In all, 7 doses of *T. inchonensis* were given between mid January and mid August.

Conclusion: *T. inchonensis* preparation was effective to reduce sarcoid lesions. Over all the sarcoids were reduced by about 75%. The preparation was particularly effective when administered into the same lymph node drainage area as a lesion.

This treatment may be particularly important with this condition where there is evidence that the virus is restricted to the lesions and there is little evidence of it in the circulation (Nasir et al Res. Vet. Sci. 1997, 63: 289-290).

These results indicate that inter alia *T. inchonensis* can be used to treat common skin neoplasms associated with the presence of papilloma viruses. Indicating the present invention will be useful in the treatment of genital warts and/or dysplasia of the uterine cervix that precedes carcinoma of the cervix, for example, both of which are caused by infection by papilloma viruses.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Goronzy J J, Fulbright J W, Crowson C S, Poland G A, O'Fallon W M, Weyand C M. Value of immunological markers in predicting responsiveness to influenza vaccination in elderly individuals. J Virol 2001 December; 75(24): 12182-7

Lio D, Balistreri C R, Candore G, D'Anna C, Di Lorenzo G, Gervasi F, Listi F, Scola L, Caruso C. In vitro treatment with interleukin-2 normalizes type-1 cytokine production by lymphocytes from elderly. Immunopharmacol Immunotoxicol 2000 May; 22(2): 195-203

Solana R, Mariani E. NK and NK/T cells in human senescence. Vaccine 2000 Feb. 25; 18(16):1613-20

Ginaldi L, De Martinis M, D'Ostilio A, Marini L, Loreto M F, Quaglino D. The immune system in the elderly: III. Innate immunity. Immunol Res 1999; 20(2):117-26

Gill H S, Rutherford K J, Cross M L. Dietary probiotic supplementation enhances natural killer cell activation in the elderly: an investigation of age-related immunological changes. J Clin Immunol 2001 July; 21(4):264-71

Gill H S, Rutherford K J, Cross M L, Gopal P K. Enhancement of immunity in the elderly by dietary supplementation with the probiotic *Bifidobacterium lactis* HN019. Am. J. Clin. Nutr. 2001 December; 74(6):833-9.

de Roos N M, Katan M B. Effects of probiotic bacteria on diarrhea, lipid metabolism, and carcinogenisis; a review of papers published between 1988 and 1998. Am. J. Clin. Nutr. 2000 February; 71(2):405-11.

Sanders M E, Klaenhammer T R. Invited review; the scientific basis of *Lactobacillus acidophilus* NCFM functionally as a probiotic. J Dairy Sci 2001 February; 84(2):19-31

Kim J H, Mun Y J, Ahn S H, Park J S, Woo W H. nduction of oral tolerance to Japanese cedar pollen. Arch Pharm Res 2001 December; 24(6):557-63

Elenkov I J, Chrousos G P Stress Hormones, Th1/Th2 patterns, Pro/Anti-inflammatory Cytokines and Susceptibility to Disease. Trends Endocrinol Metab 1999 November; 10(9):359-368

Faist E, Schinkel C, Zimmer S. Update on the mechanisms of immune suppression of injury and immune modulation. World J Surg 1996 May; 20(4):454-9

Paik I H, Toh K Y, Lee C, Kim J J, Lee S J. Psychological stress may induce increased humoral and decreased cellular immunity. Behav Med 2000 Fall; 26(3):139-41

Kang D H, Fox C Th1 and Th2 cytokine responses to academic stress. Res Nurs Health 2001 August; 24(4):245-57

TABLE 4

Experimental Design. Groups of 6 weanling female outbred mice received the following treatments:

| | Day 0 | Day 7 | day 14 | Day 21 | Day 28 | day 35 | day 42 | day 49 | day 56 | day 77 | Day 84 | Day 105 |
|---|---|---|---|---|---|---|---|---|---|---|---|---|
| Group 1 | R/r | DTP | DTP | DTP | MMR | | | | BCG | | TT | |
| Group 2 | R/r | | | | DTP | DTP | DTP | MMR | | BCG | | TT |
| Group 3 | | DTP | DTP | DTP | MMR | | | | BCG | | TT | |
| Group 4 | | | | | DTP | DTP | DTP | MMR | | BCG | | TT |
| Group 5 | | | | | | | | | BCG | | TT | |
| Group 6 | | | | | R/r | | | | | BCG | | TT |
| Group 7 | | R/r/DTP | DTP | DTP | MMR | | | | BCG | | TT | |

Key
R/r *Rhodococcus ruber*
DTP Diptheria/tetanus/pertussus
MMR Measles/Mumps/Rubella
BCG BCG vaccine
TT Tuberculin Test Iwakabe k, Shimade m, Ohta A, Yahata T, Ohmi Y, habu S, Nishimura T. The restraint stress drives a shift in Th1/Th2 balance towards Th2-dominant immunity in mice. Immunol lett 1998 May; 62(1):39-43

Mehta S K, Pierson D-L, Cooley H, Dubow R, Lugg D. Epstein-Barr virus reactivation associated with diminished cell-mediated immunity in Antarctic expeditioners. J. Med. Virol. 2000. June; 61(2);235-40

Bauer M E, Vedhara K, Perks P, Wilcock G K, Lightman S L, Shanks N. Chronic stress in caregivers of dementia patients is associated with reduced lymphocyte sensitivity to glucocorticoids. J. Neuroimmonol. 2000 feb 1; 103(1):84-92

Norbiato G, Vago T, Battocchio L. Microbial and fungal contamination contributes to physical stress in space flight: studies in the Euromir-95 mission. J Gravit Physiol 1998 July; 5(1):P145-6

Elenkov I J, Chrousos G P. Stress, cytokine patterns and susceptibility to disease. Baillieres Best Pract Res Clin Endocrinol Metab 1999 December; 13(4):583-95

Lawrence D A, Kim D. Central/peripheral nervous system and immune responses. Toxicology 2000 Jan. 17; 124(3): 189-201

The invention claimed is:

1. A pharmaceutical composition comprising isolated $10^4$ to $10^{10}$ killed whole cells of a bacterium selected from the genera *Rhodococcus, Gordonia, Dietzia*, and *Tsukamurella* and a pharmaceutically acceptable carrier, diluent or excipient, which pharmaceutical composition in use modifies a cellular immune response.

2. A pharmaceutical composition according to claim 1 wherein said composition further comprises an antigen or antigenic determinant.

3. A pharmaceutical composition according to claim 2 wherein said antigen or antigenic determinant is an antigen or antigenic determinant selected from one or more of a BCG (bacillus of Calmette and Guerin) vaccine, a diphtheria toxoid vaccine, a diphtheria/tetanus/pertussis vaccine, a pertussis vaccine, the tetanus toxoid vaccine, the measles vaccine, the mumps vaccine, the rubella vaccine, the OPV (oral poliomyelitis vaccine) and *Mycobacterium vaccae*, or part thereof.

4. A pharmaceutical composition according to claim 2 wherein said composition comprises two or more such antigens or antigenic determinants.

5. A pharmaceutical composition claim 1 wherein said bacterium is selected from the genus *Rhodococcus*.

6. A pharmaceutical composition according to claim 5 wherein said bacterium is one or more of the following *Rhodococcus ruber, Rhodococcus rhodococcus, Rhodococcus rhodnii, Rhodococcus coprophilus, Rhodococcus opacus* and *Rhodococcus erythopolis*.

7. A method for treating or preventing a condition in a subject comprising administering an effective amount of a composition comprising $10^4$ to $10^{10}$ killed whole cells of a bacterium selected from the genera *Rhodococcus, Gordonia, Dietzia, Tsukamurella* and *Nocardioides* and a pharmaceutically acceptable carrier, diluent or excipient, which composition in use modifies a cellular immune response.

8. A method for immunizing a subject comprising administering a composition comprising $10^4$ to $10^{10}$ killed whole cells of a bacterium selected from the genera *Rhodococcus, Gordonia, Dietzia, Tsukamurella* and *Nocardioides* and a pharmaceutically acceptable carrier, diluent or excipient, which composition in use modifies a cellular immune response.

9. A method according to claim 7 wherein said composition is co-administered with an antigen or antigenic determinant.

10. A method according to claim 9 wherein the antigen or antigenic determinant is an antigen or antigenic determinant selected from one or more of a BCG (bacillus of Calmette and Guerin) vaccine, a diphtheria toxoid vaccine, a diphtheria/tetanus/pertussis vaccine, a pertussis vaccine, a tetanus toxoid vaccine, a measles vaccine, a mumps vaccine, a rubella vaccine, a OPV (oral poliomyelitis vaccine) and *Mycobacterium vaccae*, or part thereof.

11. A method according to claim 9 wherein said composition is co-administered with two or more such antigens or antigenic determinants.

12. A method according to claim 8 wherein said composition is co-administered with an antigen or antigenic determinant.

13. A method according to claim 12 wherein the antigen or antigenic determinant is an antigen or antigenic determinant selected from one or more of a BCG (bacillus of Calmette and Guerin) vaccine, a diphtheria toxoid vaccine, a diphtheria/tetanus/pertussis vaccine, a pertussis vaccine, a tetanus toxoid vaccine, a measles vaccine, a mumps vaccine, a rubella vaccine, a OPV (oral poliomyelitis vaccine) and *Mycobacterium vaccae*, or part thereof.

14. A method according to claim 12 wherein said composition is co-administered with two or more such antigens or antigenic determinants.

15. A pharmaceutical composition according to claim 3 wherein said composition comprises two or more such antigens or antigenic determinants.

16. A method according to claims 7 or 8 wherein the composition is a pharmaceutical composition.

17. A method according to claims 7 or 8 wherein the composition is an immune modulator composition.

* * * * *